US012599370B2

(12) United States Patent
Uchihara

(10) Patent No.: US 12,599,370 B2
(45) Date of Patent: Apr. 14, 2026

(54) ULTRASOUND DIAGNOSTIC SYSTEM

(71) Applicant: FUJIFILM Corporation, Tokyo (JP)

(72) Inventor: Masanobu Uchihara, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 18/778,868

(22) Filed: Jul. 19, 2024

(65) Prior Publication Data

US 2024/0366191 A1 Nov. 7, 2024

Related U.S. Application Data

(63) Continuation of application No. PCT/JP2023/002498, filed on Jan. 26, 2023.

(30) Foreign Application Priority Data

Feb. 18, 2022 (JP) ................................. 2022-024080

(51) Int. Cl.
*A61B 8/00* (2006.01)
*A61B 8/12* (2006.01)
(52) U.S. Cl.
CPC .................. *A61B 8/58* (2013.01); *A61B 8/12* (2013.01); *A61B 8/4494* (2013.01)
(58) Field of Classification Search
CPC ........... A61B 8/58; A61B 8/12; A61B 8/4494; A61B 8/00; A61B 8/14; A61B 8/54; G01S 7/5205; G06T 7/00
See application file for complete search history.

(56) References Cited

U.S. PATENT DOCUMENTS

2004/0153862 A1* 8/2004 Grellmann ........... A61B 5/0022
714/43
2010/0016720 A1* 1/2010 Iwasaki .................... A61B 8/00
600/443

(Continued)

FOREIGN PATENT DOCUMENTS

CN 108464845 A 8/2018
JP S60-193447 A 10/1985

(Continued)

OTHER PUBLICATIONS

International Search Report issued in PCT/JP2023/002498; mailed Mar. 14, 2023.

(Continued)

*Primary Examiner* — Pascal M Bui Pho
*Assistant Examiner* — Michael Yiming Fang
(74) *Attorney, Agent, or Firm* — Studebaker Brackett PLLC

(57) ABSTRACT

A verification mode execution unit that executes a verification mode for verifying an operation of an ultrasound transducer array in which a plurality of ultrasound transducers are arranged includes an ultrasound image data generation unit that generates ultrasound image data of each pixel corresponding to each ultrasound transducer from a transmission and reception signal of each ultrasound transducer, and a failure channel detection unit that analyzes the generated ultrasound image data to detect a failed failure transducer channel, in which the transducer channel is a channel that includes the ultrasound transducer and that generates the ultrasound image data of the pixel, and the failure channel detection unit changes a determination criterion for determining the failure in accordance with a condition related to an influence degree on an acquired ultrasound image. As a result, provided is an ultrasound diagnostic system that can provide a mechanism for a user (Continued)

such as a medical worker and a service man who performs maintenance or inspection to detect and to notify of disconnections of the ultrasound transducer and a transmission line such as a signal line of the ultrasound transducer in a simple and automatic manner on a daily basis to specify a failure channel.

11 Claims, 8 Drawing Sheets

(56) References Cited

U.S. PATENT DOCUMENTS

| | | | | |
|---|---|---|---|---|
| 2014/0126791 A1* | 5/2014 | Iimura | | A61B 8/58 |
| | | | | 382/128 |
| 2023/0088350 A1 | 3/2023 | Iwahashi | | |

FOREIGN PATENT DOCUMENTS

| | | | | |
|---|---|---|---|---|
| JP | H09-313488 | A | | 12/1997 |
| JP | H10-262967 | A | | 10/1998 |
| JP | 2009178262 | A | * | 8/2009 |
| JP | 2011-050542 | A | | 3/2011 |
| JP | 2021-039267 | A | | 3/2021 |
| WO | 2008/035415 | A1 | | 3/2008 |
| WO | 2013/011800 | A1 | | 1/2013 |
| WO | 2022/071380 | A1 | | 4/2022 |

OTHER PUBLICATIONS

International Preliminary Report On Patentability (Chapter I) and Written Opinion of the International Searching Authority issued in PCT/JP2023/002498; issued Aug. 20, 2024.
An Office Action mailed by the Japan Patent Office on Mar. 10, 2026, which corresponds to Japanese Patent Application No. 2024-501057 and is related to U.S. Appl. No. 18/778,868; with English translation.

* cited by examiner

ULTRASOUND DIAGNOSTIC SYSTEM

CROSS-REFERENCE TO RELATED APPLICATIONS

This application is a Continuation of PCT International Application No. PCT/JP2023/002498 filed on Jan. 26, 2023, which claims priority under 35 U.S.C. § 119 (a) to Japanese Patent Application No. 2022-024080 filed on Feb. 18, 2022. The above applications are hereby expressly incorporated by reference, in their entirety, into the present application.

BACKGROUND OF THE INVENTION

1. Field of the Invention

The present invention relates to an ultrasound diagnostic system, and more particularly to an ultrasound diagnostic system capable of simply detecting a state of a channel of an ultrasound transducer of the ultrasound diagnostic system and determining whether a failure requires repair.

2. Description of the Related Art

An ultrasound diagnostic system that uses ultrasound imaging of a part to be observed of a subject, such as a human body, generally comprises an ultrasound probe for body surface (probe) that is brought into contact with the subject to be used or an ultrasound probe for body cavity that is inserted into a body cavity of the subject to be used. Furthermore, in recent years, an ultrasound endoscope in which an endoscope that optically observes the inside of the subject and the ultrasound probe for body cavity are combined is used.

An ultrasound image is acquired by transmitting an ultrasound beam to the part to be observed and receiving an ultrasound echo generated in the subject using an ultrasound probe provided with an ultrasound transducer array in which a plurality of ultrasound transducers are arranged.

In such an ultrasound diagnostic system, in order to always obtain an appropriate ultrasound image necessary for ultrasound diagnosis, it is necessary to confirm the normality of the ultrasound diagnostic system including the ultrasound probe. Therefore, it has been proposed to perform self-diagnosis of an ultrasound diagnostic system that can be performed in operation and performance tests in manufacturing and delivery of the ultrasound diagnostic system, periodic maintenance, maintenance in a case where a failure occurs, a test for confirming normality before use, and the like (see JP1997-313488A (JP-H09-313488A), JP1998-262967A (JP-H10-262967A), and JP1985-193447A (JP-S60-193447A)).

JP1997-313488A (JP-H09-313488A) discloses an ultrasound diagnostic apparatus comprising a reception unit that receives an ultrasound echo signal received by each of a plurality of ultrasound transducers of an ultrasound probe and that has a test signal generating unit for inputting a signal parallel to each ultrasound transducer, an image processing unit that processes the ultrasound echo signal to generate a diagnosis image, a display unit that displays the diagnosis image, and a self-diagnosis unit that performs self-diagnosis based on the image created by the image processing unit using a test signal. According to this configuration, it is possible to completely automatically perform self-diagnosis of the ultrasound diagnostic apparatus without requiring a special apparatus outside. That is, using the self-diagnosis image created by performing the self-diagnosis image generating processing by the image processing unit based on the test signal from the test signal generating unit, the necessary self-diagnosis can be automatically performed in the self-diagnosis unit, and the self-diagnosis result can be displayed on the display unit. Specifically, after the self-diagnosis image generating processing, the self-diagnosis unit can automatically perform encoding via the encoding unit using the brightness of the self-diagnosis image, determination of the failure location and the failure type via the determination unit, and display of the failure location and the failure type via the imaging unit. Therefore, not only a specialized maintenance person of the ultrasound diagnostic apparatus, such as a service man, but also a medical worker who actually uses the ultrasound diagnostic apparatus in a medical site can automatically perform the self-diagnosis in case of starting a system and can detect a failure of the system at an early stage in addition to capable of performing the self-diagnosis by just giving an instruction from the operating part, which is helpful in preventing erroneous diagnosis due to the failure of the system.

JP1998-262967A (JP-H10-262967A) discloses a mechanical scanning type ultrasound diagnostic apparatus comprising an ultrasound probe having a transducer, a rotation control unit that rotates the transducer in a scanning direction, a reception unit that has a unit that amplifies an echo signal received by the transducer and a test signal generating unit for inputting a test signal to a signal line connected to the transducer, an image processing unit that processes the echo signal to generate a diagnosis image, a display unit that displays the diagnosis image, a control unit that controls each unit, and a self-diagnosis unit that performs self-diagnosis. According to this configuration, it is possible to completely automatically perform self-diagnosis of the ultrasound diagnostic apparatus without requiring a special apparatus outside. The ultrasound diagnostic apparatus disclosed in JP1998-262967A (JP-H10-262967A) has a different scanning system from that of the ultrasound diagnostic apparatus disclosed in JP1997-313488A (JP-H09-313488A), but similarly, comprises a test signal generating unit for performing self-diagnosis, an encoding unit that converts a diagnosis image into a multidimensional code string based on brightness information of the diagnosis image, a determination unit that determines a failure location or a failure type, and an imaging unit that converts the failure information into a display image that can be easily recognized, and similarly, even non-experts can easily obtain the failure information.

JP1985-193447A (JP-S60-193447A) discloses an ultrasound diagnostic apparatus comprising a probe configured with a plurality of transducers, a large number of pulsers that generate a pulse for driving the transducers, a large number of first stage amplifiers that receive a reception signal from the transducers, a unit that selects any one of outputs of the first stage amplifiers and that extracts the selected output as one sound ray signal, a unit that appropriately processes and displays the output signal from the unit, and a controller that controls selection of the outputs of the pulsers and the first stage amplifiers, in which, in a test mode, each time one circuit of the pulsers is driven based on control of the controller, the output of the first stage amplifier corresponding to the pulser is selected, and thus, it is possible to determine which of a combination of the pulsers and the first stage amplifiers is defective from an abnormality of a display image to be obtained. According to this configuration, the tests of the pulser and the first stage amplifier can be easily self-diagnosed without using special jigs, oscilloscopes, and the like, and the defects of the pulser and the first stage amplifier can be easily detected through the image by only commanding the test mode to the controller, and thus, there is no need to use a special dedicated apparatus as in the related art, which is very convenient for maintenance inspection or the like on the site.

SUMMARY OF THE INVENTION

In the ultrasound diagnostic apparatuses disclosed in JP1997-313488A (JP-H09-313488A), JP1998-262967A (JP-H10-262967A), and JP1985-193447A (JP-S60-193447A), it is possible to automatically perform self-diagnosis, so that it is possible to specify a failure location, a failure type, and the like and to easily recognize failure information. However, the failure information to be specified is on an abnormality of a multiplexer, a disconnection of a signal line from the multiplexer to the cross-point switch, a disconnected signal line existing in a plurality of signal lines connected from the cross-point switch to the delay unit, a short circuit of a signal line between the transducer groups and the multiplexer groups, or the like in the apparatus disclosed in JP1997-313488A (JP-H09-313488A), on a failure such as a disconnection in a circuit system of a reception unit, a gain defect (abnormality) of the reception unit, a failure of a reception system, a failure of the variable gain amplifier 10, a failure of the preamplifier 9, or the like in the apparatus disclosed in JP1998-262967A (JP-H10-262967A), and on a defect of the pulser and/or the first stage amplifier in the apparatus disclosed in JP1985-193447A (JP-S60-193447A).

Therefore, in these ultrasound diagnostic apparatuses, there is a problem in that it is not possible to specify a failure transducer channel (hereinafter, also simply referred to as a failure channel) such as a failed ultrasound transducer, a disconnected signal line, or a short-circuited signal line.

Further, since the same image processing is performed on the ultrasound diagnosis image and the failure diagnosis image, the brightness change due to the presence of the failure channel is averaged in a plurality of channels. Therefore, there is a problem in that the failure channel cannot be specified.

Therefore, in these ultrasound diagnostic apparatuses, there is a problem in that it is not possible to accurately specify the position of the failure channel, the number of failure channels, and the like, it is not possible to accurately ascertain the influence degree on the acquired ultrasound diagnosis image, and it is difficult to accurately determine the necessity or urgency of repair.

A first object of the present invention is to provide an ultrasound diagnostic system that can resolve the problems of the related art and that can provide a mechanism for a user such as a medical worker and a service man who performs maintenance or inspection to detect and to notify of disconnections of an ultrasound transducer and a transmission line such as a signal line of the ultrasound transducer in a simple and automatic manner on a daily basis to specify a failure channel.

In addition, a second object of the present invention is to provide an ultrasound diagnostic system that can actively notify of a failure channel caused by disconnections of an ultrasound transducer and a transmission line such as a signal line, which has a large influence on diagnosis, and urge repair and that can reduce a repair frequency of a failure channel having a small influence.

In addition, a third object of the present invention is to provide an ultrasound diagnostic system that can ascertain an increase in the number of disconnection lines in advance and that can present the increase to a service man quickly.

In order to achieve the above objects, an ultrasound diagnostic system according to a first aspect of the present invention is an ultrasound diagnostic system that acquires an ultrasound image of a part to be observed of a subject and performs diagnosis, the ultrasound diagnostic system comprising: an ultrasound probe provided with an ultrasound transducer array in which a plurality of ultrasound transducers that irradiate the part to be observed with an ultrasonic wave and receive an echo signal from the part to be observed to output a detection signal are arranged; and a verification mode execution unit that executes a verification mode for verifying an operation of the ultrasound transducer array, in which the verification mode execution unit includes an ultrasound image data generation unit that generates ultrasound image data of each pixel corresponding to each ultrasound transducer from a transmission and reception signal of each ultrasound transducer, and a failure channel detection unit that analyzes the generated ultrasound image data to detect a failed failure transducer channel, a transducer channel is a channel that includes the ultrasound transducer and that generates the ultrasound image data of the pixel, and the failure channel detection unit changes a determination criterion for determining the failure in accordance with a condition related to an influence degree on the acquired ultrasound image.

Here, it is preferable that a notification unit that notifies of a detection result of the failure channel detection unit is further provided.

In addition, it is preferable that the determination criterion includes at least either the ultrasound image data of the pixel or the number of the transducer channels.

In addition, it is preferable that the condition is a position of the ultrasound transducer in an arrangement direction.

In addition, it is preferable that the condition is a position of the ultrasound transducer that is determined depending on an apparatus type of the ultrasound diagnostic system.

In addition, it is preferable that the number of defective transducer channels, which is the determination criterion, is smaller at a position of the ultrasound transducer at which the influence degree on the ultrasound image is large than at a position of the ultrasound transducer at which the influence degree is small.

In addition, it is preferable that the condition is at least one use mode of a user mode used by a user or a service man mode used by a service man.

In addition, it is preferable in a case where the failure is determined in each of the user mode and the service man mode, a notification is performed in each mode.

In addition, it is preferable that a memory that stores logs of the number of detected defective transducer channels, the failure transducer channel, and at least one of a date or a date and time on which the failure transducer channel is detected, or the number of times of energization of the failure transducer channel in a case where the verification mode is executed is further provided.

In addition, it is preferable that diagnostic image processing for acquiring a diagnostic ultrasound image of the part to be observed is different from failure transducer channel detection image processing for generating the ultrasound image data in a case where the verification mode is executed.

In addition, it is preferable that in the failure transducer channel detection image processing, processing across the plurality of ultrasound transducers is reduced as compared with the diagnostic image processing.

In addition, it is preferable that in the failure transducer channel detection image processing, processing across the plurality of ultrasound transducers is not performed.

According to the present invention, it is possible to provide an ultrasound diagnostic system that can provide a mechanism for a user such as a medical worker and a service man who performs maintenance or inspection to detect and to notify of disconnections of an ultrasound transducer and a transmission line such as a signal line of the ultrasound transducer in a simple and automatic manner on a daily basis to specify a failure channel.

In addition, according to the present invention, it is possible to provide an ultrasound diagnostic system that can actively notify of a failure channel caused by disconnections of an ultrasound transducer and a transmission line such as a signal line, which has a large influence on diagnosis, and urge repair and that can reduce a repair frequency of a failure channel having a small influence.

In addition, according to the present invention, it is possible to provide an ultrasound diagnostic system that can ascertain an increase in the number of disconnection lines in advance and that can present the increase to a service man quickly.

BRIEF DESCRIPTION OF THE DRAWINGS

FIG. 4 is a block diagram showing the configuration of an ultrasound processor device shown in FIG. 1.

DESCRIPTION OF THE PREFERRED EMBODIMENTS

An ultrasound diagnostic system according to an embodiment of the present invention will be described in detail below based on preferred embodiments shown in the accompanying diagrams.

The present embodiment is a representative embodiment of the present invention, but is merely an example and does not limit the present invention.

In addition, in the present specification, a numerical range represented using "to" means a range including numerical values described before and after the preposition "to" as a lower limit value and an upper limit value.

<<Outline of Ultrasound Diagnostic System>>

Figure 1:
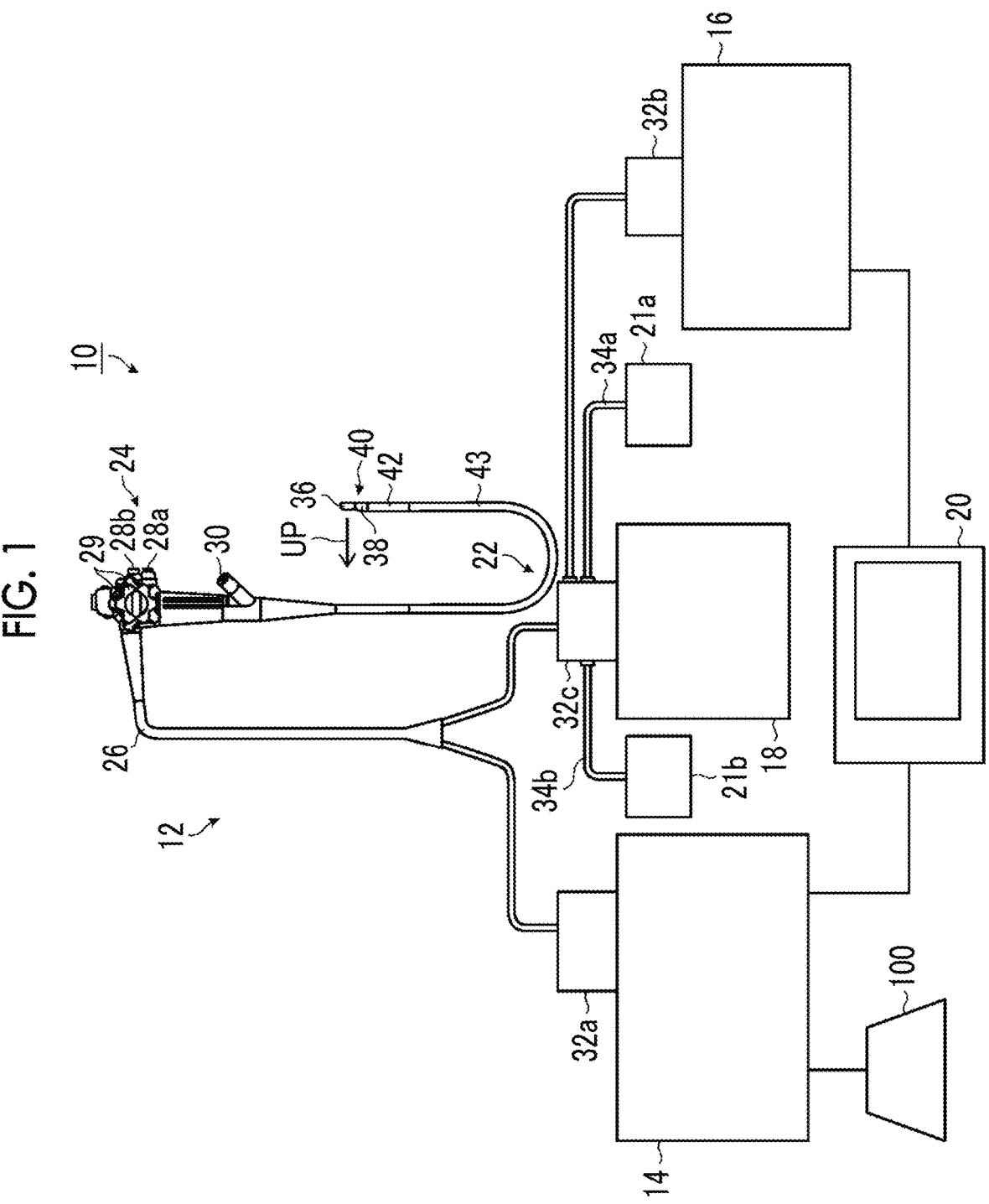
FIG. 1 is a diagram showing the schematic configuration of an ultrasound diagnostic system according to an embodiment of the present invention.

The outline of an ultrasound diagnostic system 10 according to the present embodiment will be described with reference to FIG. 1. FIG. 1 is a diagram showing the schematic configuration of the ultrasound diagnostic system 10.

The ultrasound diagnostic system 10 is used to acquire an ultrasound image or to evaluate a state of a part to be observed in a body of a patient as a subject to perform diagnosis (hereinafter, also referred to as ultrasound diagnosis) using ultrasonic waves.

Here, the part to be observed is a part (observation target part) where it is difficult to perform an examination from the body surface side of a subject such as a patient, and in particular, for example, an organ such as a gallbladder or a pancreas. In a case of these organs, with the use of the ultrasound diagnostic system 10, it is possible to perform ultrasound diagnosis of a state of the part to be observed and the presence or absence of an abnormality by way of digestive tracts, such as esophagus, stomach, duodenum, small intestine, and large intestine, which are body cavities of the patient.

The part to be observed to be diagnosis target by the ultrasound diagnostic system 10 is not limited to these organs, and may be digestive tracts, such as esophagus, stomach, duodenum, small intestine, or large intestine, which are body cavities of the patient, or a heart, a kidney, or other organs.

Hereinafter, the ultrasound diagnostic system 10 will be described as having a function of performing the ultrasound diagnosis and a function of acquiring an endoscope image. However, in the present invention, the ultrasound diagnostic system 10 may not have a function of acquiring the endoscope image, but may have only a function of performing the ultrasound diagnosis and may perform only the ultrasound diagnosis. That is, the ultrasound diagnostic system 10 according to the embodiment of the invention may be an ultrasound diagnostic system that does not need to have an ultrasound endoscope 12 comprising an ultrasound observation portion 36 and an endoscope observation portion 38, which will be described later, that does not have the endoscope observation portion 38 and a light source device 18 required for acquiring an endoscope image and components required for only endoscope observation, and that has the ultrasound observation portion 36 for acquiring the ultrasound image and components required for only ultrasound observation.

Further, in a case where the ultrasound diagnostic system 10 has only a function of performing the ultrasound diagnosis and performs only the ultrasound diagnosis, the ultrasound diagnostic system 10 can observe and evaluate the state of the part to be observed of the subject from the body surface side of the subject and perform the diagnosis. Examples of the part to be observed of the subject that can be observed from the body surface side of the subject, that is, where the state can be evaluated and/or diagnosed include tissues on the body surface side of the subject, for example, body surface blood vessels, veins, arteries, or a thyroid gland, and tissues in the body that can be observed from the body surface side, for example, digestive tracts, such as esophagus, stomach, duodenum, small intestine, or large intestine, or a heart, a kidney, or the like.

The ultrasound diagnostic system 10 acquires an ultrasound image and an endoscope image, and as shown in FIG. 1, has the ultrasound endoscope 12, an ultrasound processor device 14, the endoscope processor device 16, the light source device 18, a monitor 20, a water supply tank 21a, a suction pump 21b, and a console 100.

Figure 2:
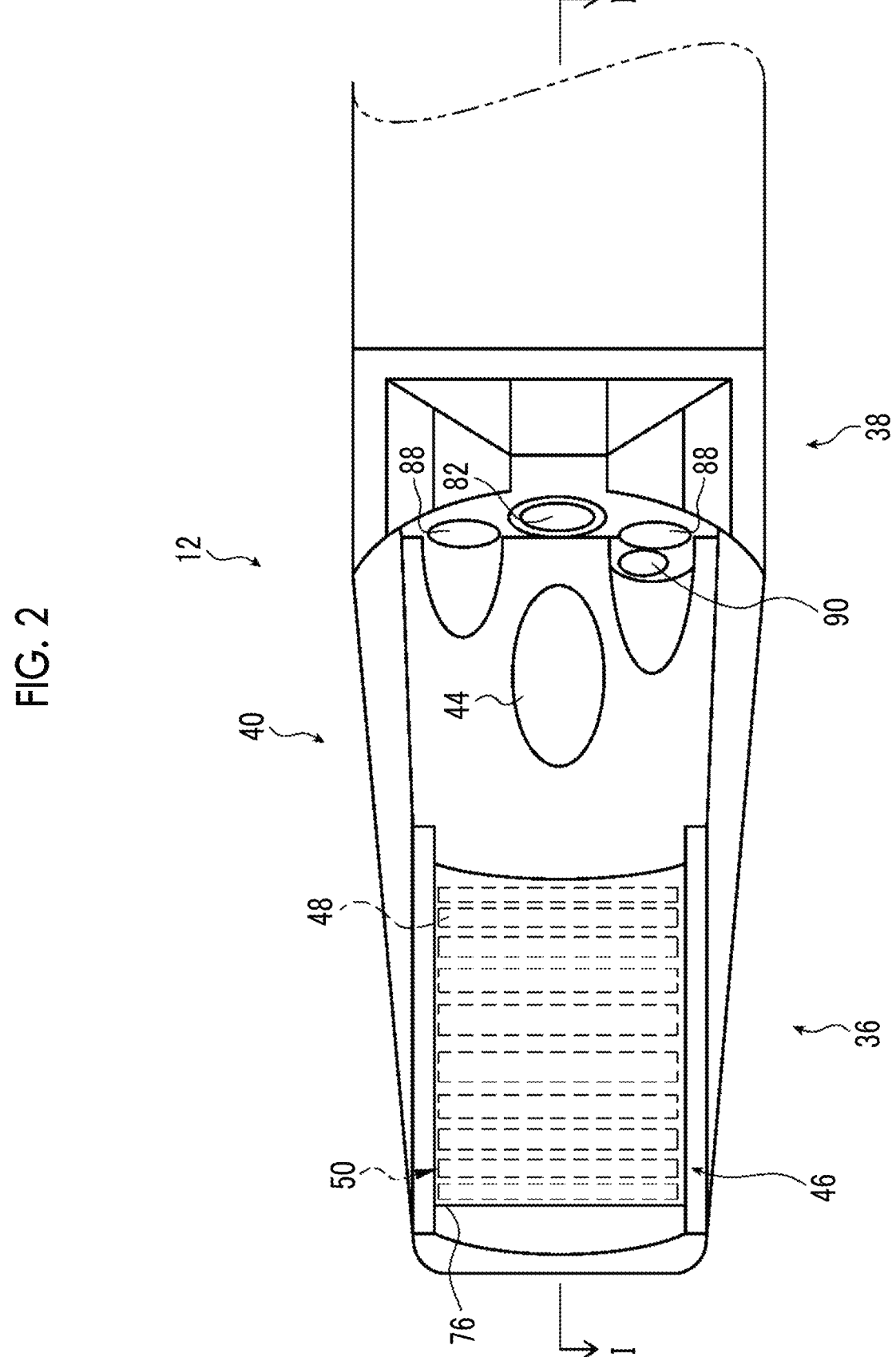
FIG. 2 is a plan view showing a distal end portion of an insertion part of an ultrasound endoscope and its periphery shown in FIG. 1.
Figure 3:
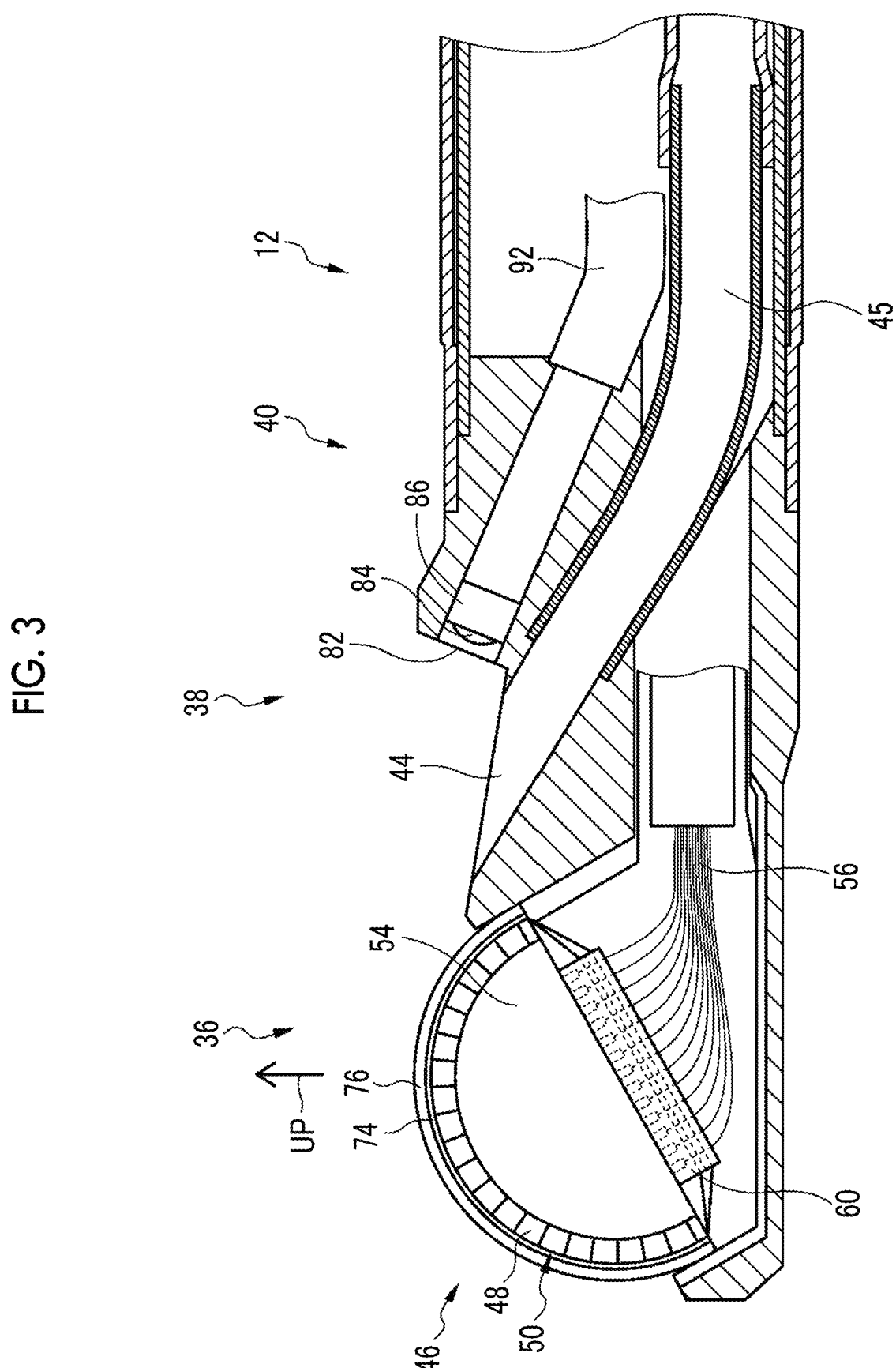
FIG. 3 is a diagram showing a cross section of the distal end portion of the insertion part of the ultrasound endoscope shown in FIG. 2 taken along line I-I in FIG. 2.

The ultrasound endoscope 12 is an endoscope, and comprises an insertion part 22 to be inserted into the body cavity of a patient, an operating part 24 operated by a doctor (user), and an ultrasound probe 46 attached to a distal end portion 40 of the insertion part 22 (refer to FIGS. 2 and 3). The operator acquires the endoscope image of the body cavity inner wall of the patient, the ultrasound image of the part to be observed, or the detection result of the failure transducer channel based on the ultrasound image data of each pixel for verifying the operation of the ultrasound transducer array 50 (refer to FIGS. 2 and 3) of the ultrasound probe 46, with the function of the ultrasound endoscope 12.

Here, the "endoscope image" is an image that is obtained by imaging the body cavity inner wall of the patient using an optical method. In addition, the "ultrasound image" is an image obtained by receiving a reflected wave (echo) of an ultrasonic wave transmitted from a body cavity of a patient to a part to be observed, or a reflected wave (echo) of an ultrasonic wave transmitted from the body cavity of the patient to air or to a liquid such as water to verify the operation of ultrasound transducer array 50, and by imaging the reception signal.

The ultrasound endoscope 12 will be described below in detail.

The ultrasound processor device 14 is connected to the ultrasound endoscope 12 through a universal cord 26 and an ultrasound connector 32a provided at an end portion of the universal cord 26. The ultrasound processor device 14 transmits an ultrasonic wave such as a verification ultrasonic wave for verifying the operation of the ultrasound transducer array 50 (see FIGS. 2 and 3). In addition, the ultrasound processor device 14 generates an ultrasound image by imaging the reception signal in a case where the reflected wave (echo) of the transmitted ultrasonic wave is received by the ultrasound probe 46, or generates ultrasound image data of each pixel corresponding to each of a plurality of ultrasound transducers 48 arranged in the ultrasound transducer array 50 from the received detection signal and analyzes the ultrasound image data of each pixel to detect a failure transducer channel.

The ultrasound processor device 14 will be described in detail later.

The endoscope processor device 16 is connected to the ultrasound endoscope 12 through the universal cord 26 and an endoscope connector 32b provided at an end portion of the universal cord 26. The endoscope processor device 16 generates an endoscope image by acquiring image data of an observation target adjacent part imaged by the ultrasound endoscope 12 (more specifically, a solid-state imaging element 86 to be described later) and performing predetermined image processing on the acquired image data.

Here, the "observation target adjacent part" is a portion that is at a position adjacent to the part to be observed in the body cavity inner wall of the patient.

In the present embodiment, the ultrasound processor device 14 and the endoscope processor device 16 are formed by two devices (computers) provided separately. However, the present invention is not limited thereto, and both the ultrasound processor device 14 and the endoscope processor device 16 may be formed by one device.

The light source device 18 is connected to the ultrasound endoscope 12 through the universal cord 26 and a light source connector 32c provided at the end portion of the universal cord 26. The light source device 18 emits white light or specific wavelength light formed of three primary color light components of red light, green light, and blue light in a case of imaging the observation target adjacent part using the ultrasound endoscope 12. The light emitted from the light source device 18 propagates through the ultrasound endoscope 12 through a light guide (not shown) included in the universal cord 26, and is emitted from the ultrasound endoscope 12 (more specifically, an illumination window 88 to be described later). As a result, the observation target adjacent part is illuminated with the light from the light source device 18.

The monitor 20 is connected to the ultrasound processor device 14 and the endoscope processor device 16, and displays an ultrasound image generated by the ultrasound processor device 14 and an endoscope image generated by the endoscope processor device 16. As a display method of the ultrasound image and the endoscope image, either one of the images may be switched and displayed on the monitor 20, or both the images may be displayed at the same time. Display modes of the ultrasound image and the endoscope image will be described later.

In the present embodiment, although the ultrasound image and the endoscope image are displayed on one monitor 20, a monitor for ultrasound image display and a monitor for endoscope image display may be provided separately. In addition, the ultrasound image and the endoscope image may be displayed in a display form other than the monitor 20. For example, the ultrasound image and the endoscope image may be displayed on a display of a terminal carried by the operator.

Figure 4:
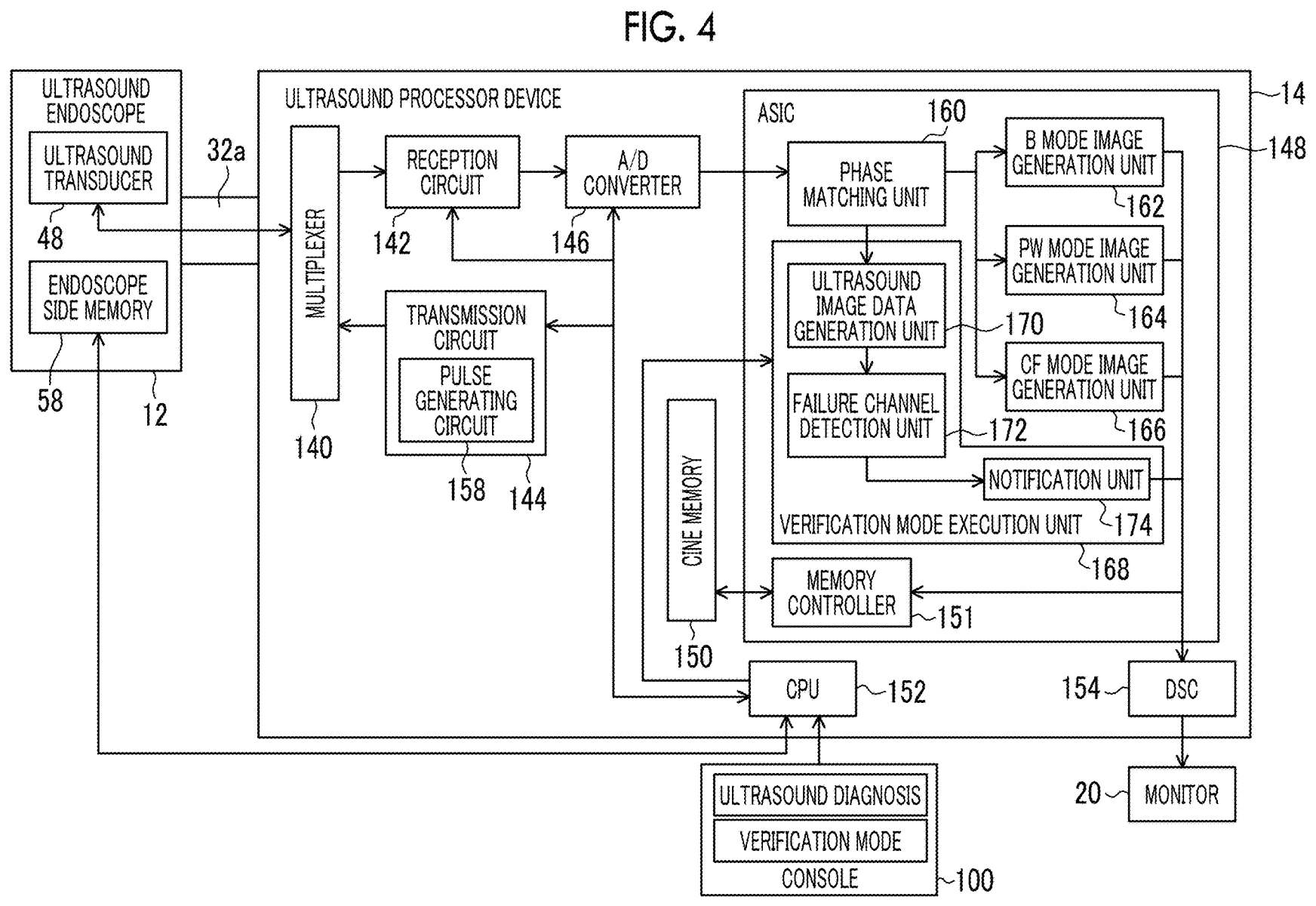

The console 100 is a device provided for the operator to input information necessary for ultrasound diagnosis or for the operator to instruct the ultrasound processor device 14 to start ultrasound diagnosis or to execute a verification mode for verifying the operation of the ultrasound transducer array 50 (see FIGS. 2 and 3) (see FIG. 4). The console 100 is configured to include, for example, a keyboard, a mouse, a trackball, a touch pad, and a touch panel. In a case where the console 100 is operated, a CPU (control circuit) 152 (refer to FIG. 4) of the ultrasound processor device 14 controls each unit of the device (for example, a reception circuit 142 and a transmission circuit 144 to be described later) according to the operation content.

Specifically, the operator inputs examination information (for example, examination order information including a date, an order number, and the like, patient information including a patient ID, a patient name, and the like, and information on an examination content and an examination target part) through the console 100 before starting the ultrasound diagnosis. In a case where the operator gives an instruction to start the ultrasound diagnosis through the console 100 after the input of the examination information is completed, the CPU 152 of the ultrasound processor device 14 controls each unit of the ultrasound processor device 14 so that the ultrasound diagnosis is performed based on the input examination information.

In addition, the operator inputs verification information indicating whether all ultrasound transducers are to be verification targets among the plurality of ultrasound transducers of the ultrasound transducer array 50, or indicating a position, the number, or the like of specific ultrasound transducers selected by the multiplexer 140 (see FIG. 4) to the console 100 before starting the verification mode. In a case where the operator gives an instruction to start the verification mode through the console 100 after the input of the verification information is completed, the CPU 152 of the ultrasound processor device 14 controls each unit of the ultrasound processor device 14 so that the verification mode is executed based on the input verification information. The details of the verification mode, which is a feature of the present invention, will be described later.

Furthermore, the operator can set various control parameters through the console 100 in executing ultrasound diagnosis. As the control parameters, for example, a selection result of a live mode and a freeze mode, a set value of a display depth (depth), a selection result of an ultrasound image generation mode, and the like are exemplified.

Here, the "live mode" is a mode where ultrasound images (moving image) obtained at a predetermined frame rate are displayed successively (displayed in real time). The "freeze mode" is a mode in which an image (still image) of one frame of an ultrasound image (moving image) generated in the past is read out from a cine memory 150 to be described later and displayed.

There are a plurality of ultrasound image generation modes that can be selected in the present embodiment. Specifically, there are a brightness (B) mode, a color flow (CF) mode, and a pulse wave (PW) mode. The B mode is a mode in which a tomographic image is displayed by converting the amplitude of the ultrasound echo into a brightness. The CF mode is a mode where an average blood flow speed, flow fluctuation, intensity of a flow signal, flow power, or the like are mapped to various colors and superimposedly displayed on a B mode image. The PW mode is a mode in which the speed (for example, speed of blood flow) of the ultrasound echo source detected based on the transmission and reception of the pulse wave is displayed.

The above-described ultrasound image generation modes are merely an example, and modes other than the above-described three kinds of modes, for example, an amplitude (A) mode, a motion (M) mode, a contrast mode, and a elastography mode may be further included or a mode in which a Doppler image is obtained may be included.

<<Configuration of Ultrasound Endoscope 12>>

Next, the configuration of the ultrasound endoscope 12 will be described with reference to FIG. 1 described above, and FIGS. 2 to 4. FIG. 2 is an enlarged plan view showing a distal end portion of an insertion part 22 of an ultrasound endoscope 12 and the periphery thereof. FIG. 3 is a cross-sectional view showing a cross section of the distal end portion 40 of the insertion part 22 of the ultrasound endoscope 12 taken along line I-I in FIG. 2.

As described above, the ultrasound endoscope 12 has the insertion part 22 and the operating part 24. As shown in FIG. 1, the insertion part 22 comprises the distal end portion 40, a bendable portion 42, and a soft portion 43 in order from the distal end side (free end side). As shown in FIG. 2, the ultrasound observation portion 36 and the endoscope observation portion 38 are provided in the distal end portion 40. As shown in FIG. 3, the ultrasound probe 46 comprising a plurality of ultrasound transducers 48 is arranged in the ultrasound observation portion 36.

Furthermore, as shown in FIG. 2, a treatment tool outlet port 44 is provided in the distal end portion 40. The treatment tool outlet port 44 serves as an outlet of a treatment tool (not shown), such as forceps, a puncture needle, or a high frequency scalpel. In addition, the treatment tool outlet port 44 serves as a suction port in the case of sucking aspirates, such as blood and body waste.

The bendable portion 42 is a portion consecutively provided on a proximal end side (a side opposite to a side on which the ultrasound probe 46 is provided) than the distal end portion 40, and is freely bent. The soft portion 43 is a portion connecting the bendable portion 42 and the operating part 24 to each other, has flexibility, and is provided so as to extend in an elongated state.

A plurality of pipe lines for air and water supply and a plurality of pipe lines for suction are formed inside each of the insertion part 22 and the operating part 24. In addition, a treatment tool channel 45 whose one end communicates with the treatment tool outlet port 44 is formed in each of the insertion part 22 and the operating part 24.

Next, the ultrasound observation portion 36, the endoscope observation portion 38, the water supply tank 21a, the suction pump 21b, and the operating part 24 among the components of the ultrasound endoscope 12 will be described in detail.

(Ultrasound Observation Portion)

The ultrasound observation portion 36 is a portion that is provided to acquire ultrasound image data and/or an ultrasound image, and is arranged on the distal end side in the distal end portion 40 of the insertion part 22. As shown in FIG. 3, the ultrasound observation portion 36 comprises the ultrasound probe 46, a plurality of coaxial cables 56, and a flexible printed circuit (FPC) 60.

The ultrasound probe 46 corresponds to an ultrasound probe (ultrasound transducer unit), and in ultrasound diagnosis, transmits ultrasonic waves using an ultrasound transducer array 50, in which a plurality of ultrasound transducers 48 described below are arranged, inside a body cavity of a patient, receives reflected waves (echoes) of the ultrasonic waves reflected by the part to be observed, and outputs reception signals. The ultrasound probe 46 according to the present embodiment is a convex type, and transmits an ultrasonic wave radially (in an arc shape). However, the type (model) of the ultrasound probe 46 is not particularly limited, and other types may be used as long as it is possible to transmit and receive ultrasonic waves. For example, a sector type, a linear type, and a radial type may be used. Therefore, the ultrasound endoscope 12 shown in FIGS. 2 and 3 is a convex type (convex scanning type) ultrasound endoscope, but the present invention is not limited to this, and may be a linear type (linear electronic scanning type) ultrasound endoscope, a sector type (electronic sector scanning type) ultrasound endoscope, or a radial type ultrasound endoscope. The ultrasound diagnostic system using the radial type ultrasound endoscope will be described below.

As shown in FIG. 3, the ultrasound probe 46 is formed by laminating a backing material layer 54, the ultrasound transducer array 50, an acoustic matching layer 74, and an acoustic lens 76.

The ultrasound transducer array 50 has a plurality of ultrasound transducers 48 arranged in a one-dimensional array. More specifically, the ultrasound transducer array 50 is formed by arranging N (for example, N=128) ultrasound transducers 48 at equal intervals in a convex bending shape along the axial direction of the distal end portion 40 (longitudinal axis direction of the insertion part 22). The ultrasound transducer array 50 may be one in which a plurality of ultrasound transducers 48 are arranged in a two-dimensional array.

Each of the N ultrasound transducers 48 is formed by arranging electrodes on both surfaces of a single crystal transducer that is a piezoelectric element. As the single crystal transducer, any of quartz, lithium niobate, lead magnesium niobate (PMN), lead magnesium niobate-lead titanate (PMN-PT), lead zinc niobate (PZN), lead zinc niobate-lead titanate (PZN-PT), lead indium niobate (PIN), lead titanate (PT), lithium tantalate, langasite, and zinc oxide can be used.

The piezoelectric element constituting the ultrasound transducer 48 used in the present invention is not limited to the above-mentioned single crystal transducer. In the present invention, as the piezoelectric element, for example, ceramics (a sintered body obtained by heating and sintering an inorganic substance or a polycrystalline material) such as lead zirconate titanate (PZT) may be used, or an organic piezoelectric material such as polyvinylidene fluoride (PVDF) may be used.

The electrodes have an individual electrode (not shown) individually provided for each of a plurality of ultrasound transducers 48 and a transducer ground (not shown) common to a plurality of ultrasound transducers 48. In addition, the electrodes are electrically connected to the ultrasound processor device 14 through the coaxial cable 56 and the FPC 60.

The ultrasound transducer 48 according to the present embodiment needs to be driven (vibrated) at a relatively high frequency of 7 MHz to 8 MHz level in order to acquire an ultrasound image in the body cavity of the patient. For this reason, the thickness of the piezoelectric element forming the ultrasound transducer 48 is designed to be relatively small. For example, the thickness of the piezoelectric element forming the ultrasound transducer 48 is 75 μm to 125 μm, preferably 90 μm to 110 μm.

A diagnostic driving pulse that has a pulsed driving voltage is supplied from the ultrasound processor device 14 to each ultrasound transducer 48, as an input signal (transmission signal), through the coaxial cable 56. In a case where the driving voltage is applied to the electrodes of the ultrasound transducer 48, the piezoelectric element expands and contracts to drive (vibrate) the ultrasound transducer 48. As a result, a pulsed ultrasonic wave is output from the ultrasound transducer 48. In this case, the amplitude of the ultrasonic wave output from the ultrasound transducer 48 has magnitude according to intensity (output intensity) in a case where the ultrasound transducer 48 outputs the ultrasonic wave. Here, the output intensity is defined as the magnitude of the sound pressure of the ultrasonic wave output from the ultrasound transducer 48.

Each ultrasound transducer 48 vibrates (is driven) with reception of a reflected wave (echo) of the ultrasonic wave, and the piezoelectric element of each ultrasound transducer 48 generates an electric signal.

The electric signal generated by each ultrasound transducer 48 is output from each ultrasound transducer 48 to the ultrasound processor device 14 as a reception signal of the ultrasonic wave. In this case, the magnitude (voltage value) of the electric signal output from the ultrasound transducer 48 has a magnitude corresponding to the reception sensitivity in a case where the ultrasound transducer 48 receives the ultrasonic wave. Here, the reception sensitivity is defined as a ratio of the amplitude of the electric signal, which is output from the ultrasound transducer 48 in response to reception of the ultrasonic wave, to the amplitude of the ultrasonic wave transmitted by the ultrasound transducer 48.

In the present embodiment, the N ultrasound transducers 48 are driven sequentially by an electronic switch, such as a multiplexer 140 (see FIG. 4), scanning with ultrasonic waves is performed in a scanning range along a curved surface on which the ultrasound transducer array 50 is arranged, for example, a range of about several tens of mm from the center of curvature of the curved surface. More specifically, in the case of acquiring a B mode image (tomographic image) as an ultrasound image, a driving voltage is supplied to m (for example, m=N/2) ultrasound transducers 48 (hereinafter, referred to as driving target transducers) arranged in series, among the N ultrasound transducers 48, by opening channel selection of the multiplexer 140. With this, the m driving target transducers are driven, and an ultrasonic wave is output from each driving target transducer of the opening channel. The ultrasonic waves output from the m driving target transducers are immediately composed, and the composite wave (ultrasound beam) is transmitted toward the part to be observed. Thereafter, each of the m driving target transducers receives an ultrasonic wave (echo) reflected at the part to be observed, and outputs an electric signal (reception signal) corresponding to the reception sensitivity at that point in time.

Then, the above-described series of steps (that is, the supply of the driving voltage, the transmission and reception of the ultrasonic waves, and the output of the electric signal) are repeatedly performed while shifting the positions of the driving target transducers among the N ultrasound transducers 48 one by one (one ultrasound transducer 48 at a time). Specifically, the above-described series of steps are started from the driving target transducers of the ultrasound transducer 48 located at one end among the N ultrasound transducers 48. Then, the above-described series of steps are repeated with the center positions of the driving target transducers to be shifted one by one (one ultrasound transducer 48 at a time) to the other end side due to switching of the opening channel by the multiplexer 140. Finally, the above-described series of steps are repeatedly performed a total of N times up to the driving target transducers of the ultrasound transducer 48 located at the other end among the N ultrasound transducers 48. The driving target transducer is essentially composed of m ultrasound transducers 48, but is composed of a certain number of ultrasound transducers 48 in accordance with the center position in a case where m ultrasound transducers 48 cannot be secured near both ends, the certain number being less than m.

The backing material layer 54 supports each ultrasound transducer 48 of the ultrasound transducer array 50 from a rear surface side. Furthermore, the backing material layer 54 has a function of attenuating ultrasonic waves propagating to the backing material layer 54 side among ultrasonic waves emitted from the ultrasound transducers 48 or ultrasonic waves (echoes) reflected by the part to be observed. The backing material is a material having rigidity, such as hard rubber, and an ultrasound attenuating material (ferrite, ceramics, and the like) is added as necessary.

The acoustic matching layer 74 is superimposed on the ultrasound transducer array 50, and is provided for acoustic impedance matching between the body of the patient and the ultrasound transducer 48. The acoustic matching layer 74 is provided, whereby it is possible to increase the transmittance of the ultrasonic wave. As a material of the acoustic matching layer 74, various organic materials of which a value of acoustic impedance is closer to that of the body of the patient than the piezoelectric element of the ultrasound transducer 48 can be used. Specific examples of the material of the acoustic matching layer 74 include epoxy resin, silicone rubber, polyimide, polyethylene, and the like.

The acoustic lens 76 superimposed on the acoustic matching layer 74 converges ultrasonic waves emitted from the ultrasound transducer array 50 toward the part to be observed. The acoustic lens 76 is formed of, for example, silicon resin (millable silicone rubber (HTV rubber), liquid silicone rubber (RTV rubber), and the like), butadiene resin, and polyurethane resin, and powders of titanium oxide, alumina, silica, and the like are mixed as necessary.

The FPC 60 is electrically connected to the electrodes of each ultrasound transducer 48. Each of the plurality of coaxial cables 56 is wired to the FPC 60 at one end thereof. Then, in a case where the ultrasound endoscope 12 is connected to the ultrasound processor device 14 through the ultrasound connector 32a, each of the plurality of coaxial cables 56 is electrically connected to the ultrasound processor device 14 at the other end (side opposite to the FPC 60 side).

(Endoscope Observation Portion)

The endoscope observation portion 38 is a portion that is provided to acquire an endoscope image, and is arranged on a proximal end side than the ultrasound observation portion 36 in the distal end portion 40 of the insertion part 22. As shown in FIGS. 2 and 3, the endoscope observation portion 38 includes an observation window 82, an objective lens 84, the solid-state imaging element 86, the illumination window 88, a cleaning nozzle 90, a wiring cable 92, and the like.

The observation window 82 is attached in a state obliquely inclined with respect to the axial direction (the longitudinal axis direction of the insertion part 22) in the distal end portion 40 of the insertion part 22. Light incident through the observation window 82 and reflected at the observation target adjacent part is formed on the imaging surface of the solid-state imaging element 86 by the objective lens 84.

The solid-state imaging element 86 photoelectrically converts reflected light of the observation target adjacent part transmitted through the observation window 82 and the objective lens 84 and formed on the imaging surface, and outputs an imaging signal. As the solid-state imaging element 86, it is possible to use a charge coupled device (CCD), a complementary metal oxide semiconductor (CMOS), and the like. The captured image signal output from the solid-state imaging element 86 is transmitted to the endoscope processor device 16 by the universal cord 26 through the wiring cable 92 extending from the insertion part 22 to the operating part 24.

The illumination windows 88 are provided at both side positions of the observation window 82. An exit end of a light guide (not shown) is connected to the illumination window 88. The light guide extends from the insertion part 22 to the operating part 24, and its incidence end is connected to the light source device 18 connected through the universal cord 26. The illumination light emitted from the light source device 18 is transmitted through the light guide and is emitted from the illumination window 88 toward the observation target adjacent part.

The cleaning nozzle 90 is an ejection hole formed in the distal end portion 40 of the insertion part 22 in order to clean the surfaces of the observation window 82 and the illumination windows 88, and air or a cleaning liquid is ejected from the cleaning nozzle 90 toward the observation window 82 and the illumination windows 88. In the present embodiment, the cleaning liquid ejected from the cleaning nozzle 90 is water, in particular, degassed water. However, the cleaning liquid is not particularly limited, and other liquids, for example, normal water (water that is not degassed) may be used.

(Water Supply Tank and Suction Pump)

The water supply tank 21a is a tank that stores degassed water, and is connected to the light source connector 32c by an air/water supply tube 34a. Degassed water is used as a cleaning liquid ejected from the cleaning nozzle 90.

The suction pump 21b sucks aspirates (including degassed water supplied for cleaning) into the body cavity through the treatment tool outlet port 44. The suction pump 21b is connected to the light source connector 32c by a suction tube 34b. The ultrasound diagnostic system 10 may comprise an air supply pump that supplies air to a predetermined air supply destination, or the like.

Inside the insertion part 22 and the operating part 24, the treatment tool channel 45 and an air/water supply pipe line (not shown) are provided.

The treatment tool channel 45 communicates a treatment tool insertion port 30 and the treatment tool outlet port 44 provided in the operating part 24. Furthermore, the treatment tool channel 45 is connected to a suction button 28b provided in the operating part 24. The suction button 28b is connected to the suction pump 21b in addition to the treatment tool channel 45.

The air/water supply pipe line communicates with the cleaning nozzle 90 on one end side, and is connected to an air/water supply button 28a provided in the operating part 24 on the other end side. The air/water supply button 28a is connected to the water supply tank 21a in addition to the air/water supply pipe line.

(Operating Part)

The operating part 24 is a portion that is operated by the operator in a case of a start of ultrasound diagnosis, during diagnosis, in a case of an end of diagnosis, and the like, and has one end to which one end of the universal cord 26 is connected. As shown in FIG. 1, the operating part 24 has the air/water supply button 28a, the suction button 28b, a pair of angle knobs 29, and a treatment tool insertion port (forceps port) 30.

In a case where each of a pair of angle knobs 29 is moved rotationally, the bendable portion 42 is remotely operated to be bent and deformed. By this deformation operation, the distal end portion 40 of the insertion part 22 in which the ultrasound observation portion 36 and the endoscope observation portion 38 are provided can be directed in a desired direction.

The treatment tool insertion port 30 is a hole formed in order that the treatment tool (not shown), such as forceps, is inserted thereinto, and communicates with the treatment tool outlet port 44 through the treatment tool channel 45. The treatment tool inserted into the treatment tool insertion port 30 is introduced into the body cavity from the treatment tool outlet port 44 after passing through the treatment tool channel 45.

The air/water supply button 28a and the suction button 28b are two-stage switching type push buttons, and are operated to switch opening and closing of the pipe line provided inside each of the insertion part 22 and the operating part 24.

<<Configuration of Ultrasound Processor Device>>

The ultrasound processor device 14 causes the ultrasound probe 46 to transmit and receive ultrasonic waves in a case where the ultrasound diagnosis is selected on the console 100, and in the ultrasound diagnosis, generates an ultrasound image by imaging the reception signal, which is output from the ultrasound transducers 48 (specifically, the driving target transducers) in a case of ultrasonic wave reception, and displays the generated ultrasound image on the monitor 20.

In a case where the verification mode is selected on the console 100, the ultrasound processor device 14 generates ultrasound image data of each pixel corresponding to each ultrasound transducer 48 from the detection signal output by each ultrasound transducer 48 in a case of receiving an ultrasonic wave, analyzes the generated ultrasound image data to detect a failed transducer channel, and notifies of the detection result through the monitor 20 or the like.

As shown in FIG. 4, the ultrasound processor device 14 has the multiplexer 140, the reception circuit 142, the transmission circuit 144, an A/D converter 146, an application specific integrated circuit (ASIC) 148, the cine memory 150, the central processing unit (CPU) 152, and a digital scan converter (DSC) 154.

The reception circuit 142 and the transmission circuit 144 are electrically connected to the ultrasound transducer array 50 of the ultrasound endoscope 12. The multiplexer 140 selects a maximum of m driving target transducers from the N ultrasound transducers 48, and opens their channels.

The transmission circuit 144 has a field programmable gate array (FPGA), a pulser (pulse generating circuit 158), a switch (SW), and the like, and is connected to the multiplexer 140 (MUX). Instead of the FPGA, an application specific integrated circuit (ASIC) may be used.

The transmission circuit 144 is a circuit that supplies a driving voltage for ultrasonic wave transmission to the driving target transducers selected by the multiplexer 140 in response to a control signal sent from the CPU 152 for transmission of ultrasonic waves from the ultrasound probe 46. The driving voltage is a pulsed voltage signal (transmission signal), and is applied to the electrodes of the driving target transducers through the universal cord 26 and the coaxial cable 56.

The transmission circuit 144 has the pulse generating circuit 158 that generates a transmission signal based on the control signal. Under the control of the CPU 152, the transmission circuit 144 generates a transmission signal for driving a plurality of ultrasound transducers 48 to generate ultrasonic waves using the pulse generating circuit 158 and supplies the transmission signal to a plurality of ultrasound transducers 48.

In addition, under the control of the CPU 152, in the case of performing ultrasound diagnosis, the transmission circuit 144 generates an ultrasound generating transmission signal having a driving voltage for performing ultrasound diagnosis using the pulse generating circuit 158.

In addition, under the control of the CPU 152, in the case of executing the verification mode, the transmission circuit 144 generates an ultrasound generating transmission signal having a driving voltage for executing the verification mode using the pulse generating circuit 158.

Here, the ultrasound generating transmission signal in a case where the verification mode is executed may be the same transmission signal as the ultrasound generating transmission signal in a case where the ultrasound diagnosis is performed, or may be a test transmission signal dedicated to executing the verification mode.

The reception circuit 142 is a circuit that receives an electric signal output from the driving target ultrasound transducer 48 that has received an ultrasonic wave (echo), that is, a reception signal.

In addition, according to the control signal sent from the CPU 152, the reception circuit 142 amplifies the reception signal received from the ultrasound transducer 48 and transmits the amplified signal to the A/D converter 146. The A/D converter 146 is connected to the reception circuit 142, and converts the reception signal received from the reception circuit 142 from an analog signal to a digital signal and outputs the converted digital signal to the ASIC 148.

The ASIC 148 is connected to the A/D converter 146. As shown in FIG. 4, the ASIC 148 forms a phase matching unit 160, a B mode image generation unit 162, a PW mode image generation unit 164, a CF mode image generation unit 166, a verification mode execution unit 168, and a memory controller 151.

In the present embodiment, the above-described functions (specifically, the phase matching unit 160, the B mode image generation unit 162, the PW mode image generation unit 164, the CF mode image generation unit 166, the verification mode execution unit 168, and the memory controller 151) are realized by a hardware circuit, such as the ASIC 148. However, the present invention is not limited thereto. The above-described functions may be realized by making the central processing unit (CPU) and software (computer program) for executing various kinds of data processing cooperate with each other.

The phase matching unit 160 executes processing of giving a delay time to the reception signals (reception data) digitized by the A/D converter 146 and performing phasing addition (performing addition after matching the phases of the reception data). By the phasing addition processing, a sound ray signal with narrowed focus of the ultrasound echo is generated.

The B mode image generation unit 162, the PW mode image generation unit 164, and the CF mode image generation unit 166 generate an ultrasound image based on the electric signal (strictly speaking, a sound ray signal generated by phasing and adding the reception data) that is output from the driving target transducer among the plurality of ultrasound transducers 48 in a case where the ultrasound probe 46 receives the ultrasonic wave (echo).

The B mode image generation unit 162 is an image generation unit that generates a B mode image as a tomographic image of the inside (the inside of the body cavity) of the patient. For the sequentially generated sound ray signals, the B mode image generation unit 162 corrects the attenuation due to the propagation distance according to the depth of the reflection position of the ultrasonic wave by sensitivity time gain control (STC). The B mode image generation unit 162 performs envelope detection processing and logarithm (Log) compression processing on the corrected sound ray signal, thereby generating a B mode image (image signal).

The PW mode image generation unit 164 is an image generation unit that generates an image indicating a speed of a blood flow in a predetermined direction. The PW mode image generation unit 164 extracts a frequency component by performing fast Fourier transform on a plurality of sound ray signals in the same direction among the sound ray signals sequentially generated by the phase matching unit 160. Thereafter, the PW mode image generation unit 164 calculates the speed of blood flow from the extracted frequency component, and generates a PW mode image (image signal) indicating the calculated speed of blood flow.

The CF mode image generation unit 166 is an image generation unit that generates an image indicating information regarding a blood flow in the predetermined direction. The CF mode image generation unit 166 generates an image signal indicating information regarding the blood flow by obtaining autocorrelation of a plurality of sound ray signals in the same direction among the sound ray signals sequentially generated by the phase matching unit 160. Thereafter, based on the image signal described above, the CF mode image generation unit 166 generates a CF mode image (image signal) as a color image in which the blood flow information is superimposed on the B mode image generated by the B mode image generation unit 162.

The memory controller 151 stores the image signal generated by the B mode image generation unit 162, the PW mode image generation unit 164, or the CF mode image generation unit 166 in the cine memory 150.

The DSC 154 is connected to the ASIC 148, converts (raster conversion) the signal of the image generated by the B mode image generation unit 162, the PW mode image generation unit 164, or the CF mode image generation unit 166 into an image signal compliant with a normal television signal scanning system, executes various kinds of necessary image processing, such as gradation processing, on the image signal, and then, outputs the image signal to the monitor 20.

The cine memory 150 has a capacity for accumulating an image signal for one frame or image signals for several frames. An image signal generated by the ASIC 148 is output to the DSC 154, and is stored in the cine memory 150 by the memory controller 151. In a freeze mode, the memory controller 151 reads out the image signal stored in the cine memory 150 and outputs the image signal to the DSC 154. As a result, an ultrasound image (still image) based on the image signal read from the cine memory 150 is displayed on the monitor 20.

The CPU 152 functions as a control unit (control circuit) that controls each unit of the ultrasound processor device 14, is connected to the reception circuit 142, the transmission circuit 144, the A/D converter 146, and the ASIC 148, and controls such circuits. Specifically, the CPU 152 is connected to the console 100 and controls each unit of the ultrasound processor device 14 in accordance with the examination information, the control parameters, and the like input through the console 100 in a case where the ultrasound diagnosis is selected on the console 100 and in accordance with the verification information and the like in a case where the verification mode is selected on the console 100.

The CPU 152 automatically recognizes the ultrasound endoscope 12 based on a method, such as Plug and Play (PnP), in a case where the ultrasound endoscope 12 is connected to the ultrasound processor device 14 through the ultrasound connector 32a.

The verification mode execution unit 168 executes a verification mode for verifying the operation of the ultrasound transducer array 50 that is provided in the ultrasound probe 46 and in which the plurality of ultrasound transducers 48 are arranged, and includes an ultrasound image data generation unit 170, a failure channel detection unit 172, and a notification unit 174. In a case where the verification mode is selected on the console 100, under the control of the CPU 152, the verification mode execution unit 168 causes the transmission circuit 144 to transmit the transmission signal to the ultrasound probe 46, the ultrasound probe 46 that has received the transmission signal to emit the ultrasonic wave, receive the reflected wave (ultrasound echo), and output the detection signal, and the reception circuit 142 to receive the detection signal corresponding to each ultrasound transducer 48. As a result, the verification mode execution unit 168 generates the ultrasound image data of each pixel corresponding to each ultrasound transducer 48 based on the received detection signal of each ultrasound transducer 48 in the ultrasound image data generation unit 170, detects the failed failure transducer channel in the failure channel detection unit 172, and notifies of the detection result in the notification unit 174.

The ultrasound image may be created from the ultrasound image data generated in the ultrasound image data generation unit 170 and displayed on the monitor 20, and the failure transducer channel detected in the failure channel detection unit 172 may be illustrated or described in the displayed ultrasound image. In this case, the notification unit 174 need not be particularly provided, but the failure transducer channel may be illustrated or described in the displayed ultrasound image using the notification unit 174.

That is, in a case where the verification mode is executed in the verification mode execution unit 168, the ultrasound probe 46 of the ultrasound endoscope 12 of the ultrasound diagnostic system 10 is arranged in the air or in a liquid such as water, and the verification mode is selected on the console 100.

In the ultrasound processor device 14 in the verification mode, under the control of the CPU 152, the ultrasound generating transmission signal for executing the verification mode or the test transmission signal dedicated to executing the verification mode is transmitted from the transmission circuit 144 to all or some of the ultrasound transducers 48 selected in the multiplexer 140 among the plurality of ultrasound transducers 48 of the ultrasound transducer array 50. As a result, the ultrasonic waves are radiated from all or some of the ultrasound transducers 48 that have received the transmission signal into the air or into the liquid without being applied to the subject. In this manner, since there is no object to which the ultrasonic waves are applied in the air or in the liquid, the reflected wave (ultrasound echo) is reflected from the ultrasound probe 46 itself, for example, the acoustic lens 76 and/or the acoustic matching layer 74.

Each ultrasound transducer 48 receives each reflected wave (ultrasound echo) from the ultrasound probe 46 itself, outputs each received reflected wave (ultrasound echo) as a detection signal converted into an electric signal, and inputs the detection signal to the reception circuit 142. The reception circuit 142 receives the detection signal output from each ultrasound transducer 48.

The detection signal from each ultrasound transducer 48 received by the reception circuit 142 is input to the A/D converter 146. The A/D converter 146 converts the analog reception signal input from the reception circuit 142 into a digital signal to obtain a digital reception signal (reception data), and inputs the digital reception signal to the phase matching unit 160 of the ASIC 148. The phase matching unit 160 of the ASIC 148 performs the phasing addition processing by giving a delay time to the reception signal (reception data) to generate a sound ray signal with narrowed focus of the ultrasound echo.

The reception signal of each ultrasound transducer 48 generated as the sound ray signal in the phase matching unit 160 is input to the verification mode execution unit 168.

The reception signal of each ultrasound transducer 48 input to the verification mode execution unit 168 is input to the ultrasound image data generation unit 170.

The ultrasound image data generation unit 170 generates ultrasound image data of each pixel corresponding to each ultrasound transducer 48 from the digital reception signal (sound ray signal) of each ultrasound transducer 48.

Similarly to the B mode image generation unit 162, the PW mode image generation unit 164, and the CF mode image generation unit 166, the ultrasound image data generation unit 170 can generate ultrasound image data of each pixel corresponding to each ultrasound transducer 48 for generating an ultrasound image based on the electric signal (strictly speaking, a sound ray signal generated by phasing and adding the reception data) that is output from the driving target transducer among the plurality of ultrasound transducers 48 in a case where the ultrasound probe 46 receives the ultrasonic wave (echo).

The ultrasound image data of each pixel generated by the ultrasound image data generation unit 170 is input to the failure channel detection unit 172.

The failure channel detection unit 172 analyzes the ultrasound image data generated by the ultrasound image data generation unit 170 to detect the failed failure transducer channel.

Figure 5:
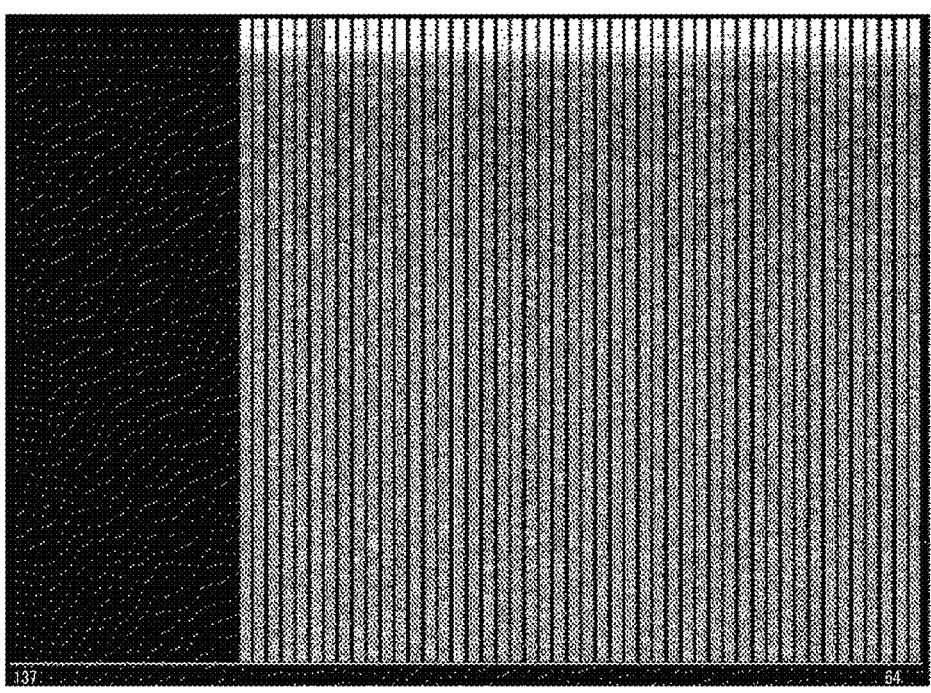
FIG. 5 is a diagram showing an image of transmission and reception of a single element for detecting a failure channel.

For example, first, in a case where an image of transmission and reception of the single element (single ultrasound transducer 48) shown in FIG. 5 is obtained from the generated ultrasound image data, using this image, in a case of the normal element (normal ultrasound transducer 48), it is possible to determine that the transducer channel is disconnected in a case where the brightness of each element having a depth of 5 mm or less is equal to or less than the threshold value by using the occurrence of multiple reflections of the acoustic lens 76 directly below the ultrasound transducer 48 by about 5 mm.

In the ultrasound image shown in FIG. 5, it can be seen that the linear transmission and reception image of the sixth ultrasound transducer 48 from the left side has a lower brightness as compared with the linear transmission and reception images of other ultrasound transducers 48, is black, and that the ultrasound transducer 48 is disconnected.

Figure 6:
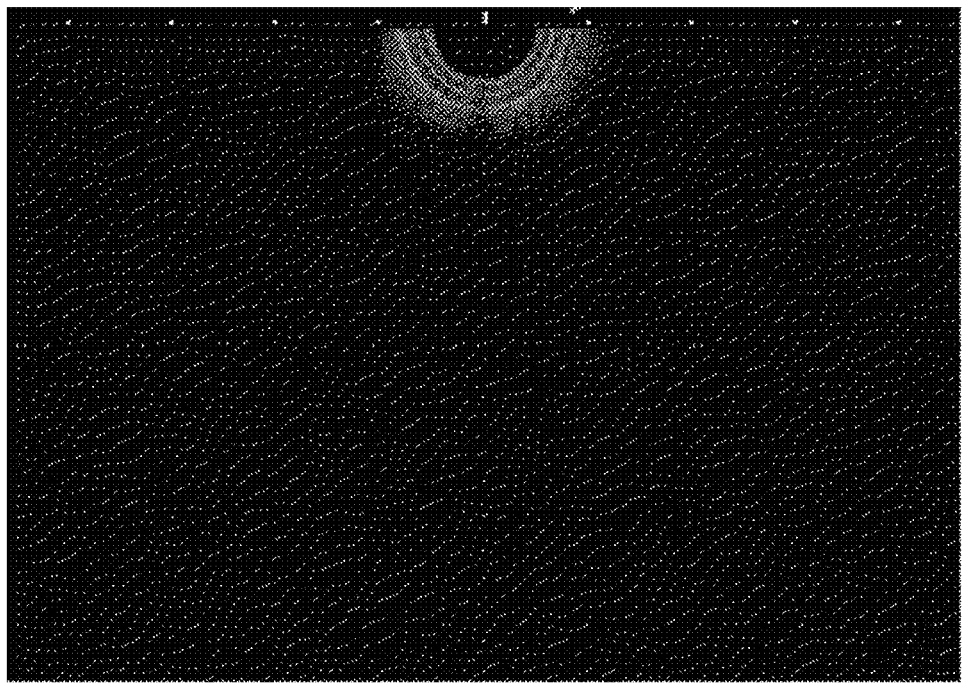
FIG. 6 is a diagram showing an image of transmission and reception of a plurality of elements for detecting a failure channel.

In addition, in a case where images of transmission and reception of the plurality of elements (the plurality of ultrasound transducers 48) shown in FIG. 6 are obtained from the generated ultrasound image data, using this image, the disconnected transducer channel can be determined from the width of the streak and the degree of decrease in brightness by using the occurrence of the vertical streak and/or the decrease in brightness in the vicinity of the disconnected element.

In the ultrasound image shown in FIG. 6, it can be seen that in the semi-arc-shaped transmission and reception images of the plurality of ultrasound transducers 48, the portion near the center of the lower side of the semi-arc has a lower brightness than other portions, is black, and that the ultrasound transducer 48 corresponding to this portion is disconnected.

The transducer channel is a channel that includes one ultrasound transducer 48 and that generates ultrasound image data of a pixel corresponding to the ultrasound transducer 48. Therefore, the transducer channel is a channel consisting of one ultrasound transducer 48 and transmission lines such as all signal lines connected to the ultrasound transducer 48.

Here, in the present invention, in a case where the failure transducer channel is detected, the failure channel detection unit 172 changes the determination criterion for determining the failure in accordance with a condition related to the influence degree on the acquired image acquired in the ultrasound diagnostic system 10.

In a case where the determination criterion is the pixel value, that is, the value (signal intensity) of the ultrasound image data of the pixel, in a case where the ultrasound probe 46 or the ultrasound endoscope 12 is caused to perform aerial radiation (transmission and reception of ultrasonic wave in the air), the determination criterion is as follows depending on whether or not the reception signal of the reflected wave from the acoustic lens 76, the acoustic matching layer 74, or the like is present as in FIGS. 5 and 6.

Normal transducer channel: the pixel value is close to white (the pixel value is high, for example, close to 255 in a case of 8 bits)

Failed transducer channel: the pixel value is close to black (the pixel value is low, for example, close to 0 in a case of 8 bits)

In a case where the beam forming processing is performed, the pixel value may be affected by the neighboring element due to the influence of the beam forming processing, but in a case of disconnection, the pixel value is considerably close to black, and in a case of decrease in sensitivity, the pixel value is close to gray.

Therefore, in the present invention, it is preferable to change the gradation threshold value of the pixel value, which is the determination criterion for determining the failed transducer channel.

Next, in a case where the determination criterion is the number of the transducer channels, a threshold value of the number of the transducer channels for determining the failure is changed according to a type, a position, or a mode of the ultrasound transducer array 50 described below.

For example, in a case of an ultrasound probe for body surface of an ultrasound diagnostic system for body surface, at an end portion (for example, 16 channels and the like at both ends) of the ultrasound probe, it is determined that there is a failure in a case where the pixel values of two or more channels are equal to or less than a predetermined pixel value, but at a central portion (for example, in a case of an ultrasound probe of 128 channels, 96 channels at the center excluding 32 (16×2) channels at left and right ends) of the ultrasound probe, it is determined that there is a failure in a case where even the pixel value of one channel is equal to or less than the predetermined pixel value.

From the above, it is preferable that the determination criterion includes at least either the ultrasound image data of the pixel or the number of the transducer channels.

In this way, it is preferable to change the determination criterion for detecting the failure between the transducer channels (16 channels at both ends) that are less likely to affect the diagnosis and the transducer channels (96 channels at the center) that are likely to affect the diagnosis.

That is, it is preferable to change the determination criterion for detecting the failure in the vicinity of the end portion, in the vicinity of the center, and in the puncture line area (in the vicinity of the center), through which the treatment tool passes, of the convex type ultrasound endoscope or the like, and in the direction (the 6 o'clock direction of the ultrasound endoscope screen, that is, the endoscope up direction (UP)) in which the observation frequency is high of the radial type ultrasound endoscope.

Figure 7:
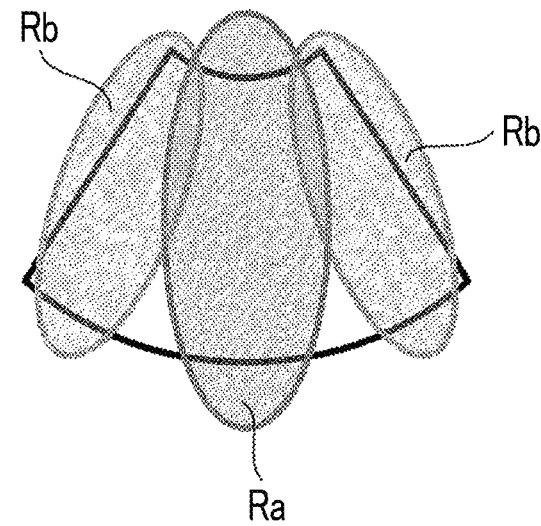
FIG. 7 is a diagram schematically showing a region that is often used for diagnosis and a region that is not used for diagnosis very much in an ultrasound probe of a convex type ultrasound endoscope.

For example, in a case of an ultrasound probe for body surface of a convex type, a linear type, or a sector type ultrasound diagnostic apparatus, or a convex type or a linear type ultrasound endoscope, as shown in FIG. 7, a region (transducer channel) Ra that is often used for diagnosis is present at the center of a fan-shaped structure of the ultrasound probe, and regions (transducer channels) Rb that are not used for diagnosis very much are present on both sides of the region (transducer channel) Ra. Therefore, in the region Ra that is often used for diagnosis, in a case where a failure is determined, it is preferable to reduce the number of disconnection lines allowed, that is, to make the determination condition strict. On the other hand, in the regions Rb on both sides that are not used for diagnosis very much, it is preferable to increase the number of disconnection lines allowed, that is, to relax the determination condition.

In this case, the number of the disconnection lines of transducer channels determined to be failed is changed between the regions Ra and Rb. For example, in a case of assuming a case of 112 channels or 128 channels in total, as described above, 1) At both end portions (for example, 16 channels at both ends), in a case where there are two disconnection lines, it can be determined that there is a failure.

2) At the central portion (for example, 80 or 96 channels at the center), in a case where there is one disconnection line, it can be determined that there is a failure.

Figure 8:
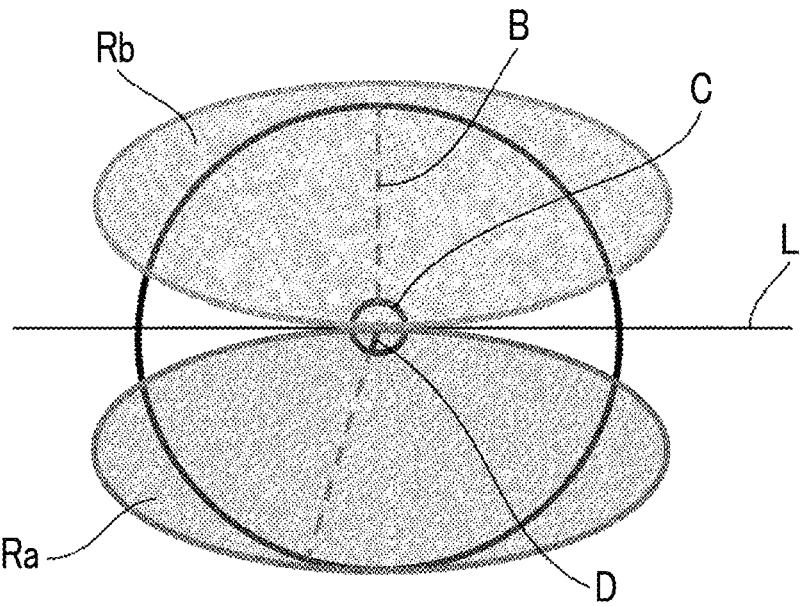
FIG. 8 is a diagram schematically showing a region that is often used for diagnosis and a region that is not used for diagnosis very much in an ultrasound probe of a radial type ultrasound endoscope.

On the other hand, in a case of the radial type ultrasound endoscope described below, as shown in FIG. 8, the region (transducer channel) Ra that is often used for diagnosis is on the lower side in the drawing, and the region (transducer channel) Rb that is not used for diagnosis very much is on the upper side. The region Ra that is often used for diagnosis and the region Rb that is not used for diagnosis very much are vertically divided by a horizontal line L that passes through an approximate center of the circular structure of the ultrasound probe. There is a line D indicating the up direction (UP) toward the lower side in the drawing in a small circle C at the center of the circular structure.

In addition, in a case of the radial type ultrasound endoscope, the image is scanned in order while being rotated to create the multi-frame image. Therefore, the cut of the image with the previous frame is always generated somewhere. However, such a cut of the image, the cut of transmission and reception, the start point, the end point, and the like are brought to the upper region Rb that is not used for the diagnosis very much. Therefore, in FIG. 8, since the region Rb is in the direction that is not much important, the cut B of the image is brought to an approximate center of the upper region Rb that is not used for the diagnosis very much.

Even in the example shown in FIG. 8, in the region Ra that is often used for diagnosis in the up direction (UP), in a case where a failure is determined, it is preferable to reduce the number of disconnection lines allowed, that is, to make the determination condition strict. On the other hand, in the region Rb that are not used for diagnosis very much in the direction opposite to the up direction (UP), it is preferable to increase the number of disconnection lines allowed, that is, to relax the determination condition. The up direction (UP) in the case of the radial type ultrasound endoscope will be described later.

That is, it is preferable that the detection threshold values (the number of disconnection lines allowed) are changed in the regions (the transducer channels) above and below the horizontal line L. It is preferable that the determination criterion be made strict in the endoscope up direction (UP), that is, in a direction in which the ultrasound image is output to be in close contact with the mucous membrane, that is, in a direction in which the observation is often performed (lower half of the circle).

In this case, the number of the disconnection lines of transducer channels determined to be failed is changed between the region Ra in the up direction (UP) and the region Rb in the direction opposite to the up direction (UP). For example, in a case of assuming a case of all 192 channels, 1) In the up direction (UP), it can be determined that there is a failure in a case where there are two disconnection lines.

2) In the direction opposite to the up direction (UP), it can be determined that there is a failure in a case where there are four disconnection lines.

From the above, it is preferable that the condition related to the influence degree on the acquired image, which causes the determination criterion for determining the failure to be changed, is the position of the ultrasound transducers 48 in the arrangement direction.

In addition, it is preferable that the condition is a position of the ultrasound transducer that is determined depending on an apparatus type of the ultrasound diagnostic system.

In addition, in the above case, it is preferable that the number of the defective transducer channels, which is the determination criterion, is smaller at a position of the ultrasound transducer 48 at which the influence degree on the ultrasound image is large than at a position of the ultrasound transducer 48 at which the influence degree is small.

In the present invention, it is preferable to prepare two types of disconnection notifications, that is, a disconnection notification for a user and a disconnection notification for a service man, and change a determination criterion of the disconnection notification. The service man can know the sign of the increase in the number of disconnection lines early via the notification of the service authority and can prepare for the countermeasure.

That is, as the condition related to the influence degree on the acquired image, it is preferable to change the determination criterion for failure in accordance with the "user mode" or the "service man mode". In addition, a "shipment inspection mode" or the like used by a factory operator at the time of product manufacturing may be added thereto.

In this case, in the user mode, the determination criterion is made more relaxed than in the service man mode.

For example, a threshold value for determining the failure can be set as follows.
Pixel Value: 50 or Less
Number of disconnection lines: 3 or more at both end portions and 2 or more at central portion On the other hand, in the service man mode, the determination criterion is made stricter than in the user mode.

For example, a threshold value for determining the failure can be set as follows.
Pixel Value: 100 or Less
Number of disconnection lines: 2 or more at both end portions and 1 or more at central portion As described above, as the condition related to the influence degree on the acquired image, it is preferable that the condition is at least one use mode of a user mode used by a user or a service man mode used by a service man.

In the present invention, in the user mode, it is preferable that a warning be issued when the NG level (determined determination criterion) that hinders the diagnosis is reached, and a notification be made to call a service man to urge repair or replacement.

It is preferable that, in the service man mode, a notification indicating that the number of failures is increasing at a level (small number of disconnection lines) before the above level is reached is issued to call the service man's attention to consideration for subsequent action. For example, by looking at this, the service man can give a repair notice to the doctor in advance.

From the above, it is preferable in a case where the failure is determined in each of the user mode and the service man mode, a notification is performed in each mode.

In the present invention, in the verification mode, by leaving logs of the failure transducer channel, the number thereof, the date or the date and time on which the failure transducer channel failed, and/or the number of times of energization, the service man can detect the tendency that the number of failure transducer channels is increasing, the relationship between the frequency of use and the failure, the future failure prediction, and the like in remote maintenance or the like.

Accordingly, it is preferable that a memory that stores logs of at least one of the number of the detected defective transducer channels, the failure transducer channel, a date or a date and time on which the failure transducer channel is detected, or the number of times of energization of the failure transducer channel in a case where the verification mode is executed is provided.

In the present invention, it is considered that the diagnostic image processing is usually applied by including a spatial filter in a lateral direction across the failure channels, for example, a noise reducing filter, in order to reduce a noise or detect an edge. Therefore, it may be difficult to visually recognize and/or detect the "streak" caused by the failure, and it may be difficult to detect the failure channel. Examples of the signal processing related to the plurality of channels that makes it difficult to detect the failure channel include moving average processing, noise reducing processing, and the like.

Therefore, the failure transducer channel detection image processing is different from the diagnostic image processing, and image processing in which processing across at least the transducer channel is reduced is preferable, and image processing in which the processing across at least the transducer channel is not performed at all is most preferable.

From the above, it is preferable that diagnostic image processing for acquiring a diagnostic ultrasound image of the part to be observed is different from failure transducer channel detection image processing for generating the ultrasound image data in a case where the verification mode is executed.

In addition, in the failure transducer channel detection image processing, as compared with the diagnostic image processing, it is more preferable that processing across the plurality of ultrasound transducers is reduced, and it is most preferable that the processing across the plurality of ultrasound transducers is not performed.

In the present invention, even in a case where the diagnostic image processing is performed as first image processing in the failure transducer channel detection image processing, it is considered that, in the verification image obtained as a result of the diagnostic image processing, the failure channel has the lowest brightness even though the failure channel does not satisfy the determination criterion. Therefore, the portion where the brightness is lowest may be regarded as the failure channel, and the failure transducer channel detection image processing may be performed in the periphery thereof without performing the processing across the plurality of transducer channels, such as the moving average. In this way, the failure channel may be specified in two stages.

Hereinafter, an ultrasound diagnostic system using the ultrasound endoscope will be described with reference to FIGS. 9 and 10.

Figure 9:
FIG. 9 is a diagram showing the schematic configuration of an ultrasound diagnostic system according to another embodiment of the present invention.

As shown in FIG. 9, the ultrasound diagnostic system 10R comprises the radial type ultrasound endoscope 12R, the ultrasound processor device 14 that generates an ultrasound image, the endoscope processor device 16 that generates an endoscope image, the light source device 18 that supplies illumination light, with which the inside of a body cavity is illuminated, to the ultrasound endoscope 12R, and/or the monitor 20 that displays the ultrasound image and the endoscope image.

Figure 10:
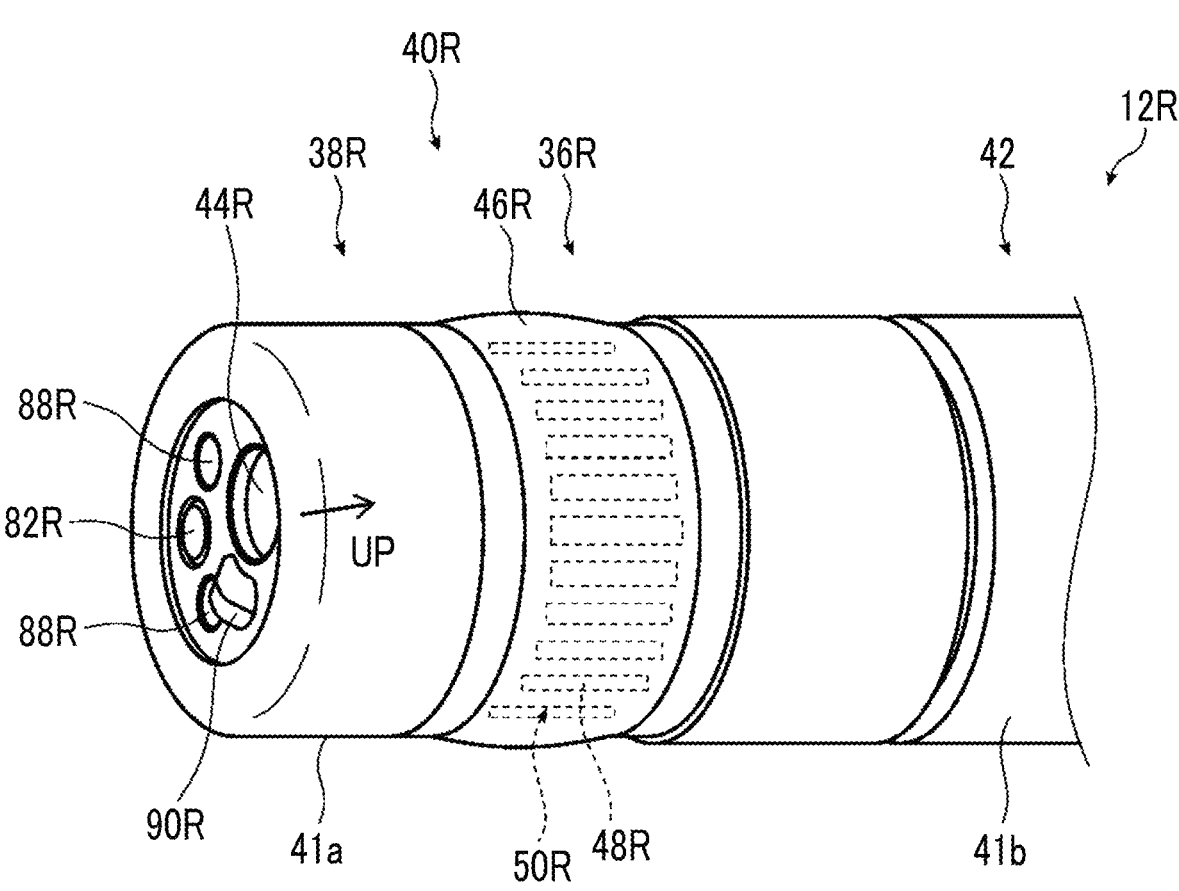
FIG. 10 is a partially enlarged perspective view showing an appearance of an example of a distal end portion of the ultrasound endoscope shown in FIG. 9.

The ultrasound diagnostic system 10R using the radial type ultrasound endoscope 12R shown in FIGS. 9 and 10 has substantially the same configuration as that of the ultrasound diagnostic system 10 using the convex type ultrasound endoscope 12 shown in FIGS. 1 to 3, except that the distal end portion 40R of the ultrasound endoscope 12R and the distal end portion 40 of the ultrasound endoscope 12 are different. Therefore, the same reference numerals are given to substantially the same configurations, and detailed description thereof will be omitted.

Further, the ultrasound diagnostic system 10R further comprises the water supply tank 21a and the suction pump 21b.

First, as shown in FIGS. 9 and 10, the ultrasound endoscope 12R according to the embodiment of the present invention has an ultrasound observation portion 36R and an endoscope observation portion 38R at a distal end portion 40R, and images the inside of a body cavity of a subject to acquire an ultrasound image (echo signal) and an endoscope image (image signal), respectively.

The ultrasound endoscope 12R comprises the endoscope observation portion 38R and the ultrasound observation portion 36R at the distal end portion 40R, and is composed of an insertion part 22R, the operating part 24, and the universal cord 26.

The air/water supply button 28a and the suction button 28b are provided side by side on the operating part 24, which is provided with the pair of angle knobs 29 and 29, the treatment tool insertion port (forceps port) 30, and the like.

The ultrasound connector 32a, the endoscope connector 32b, and the light source connector 32c are provided at the other end portion of the universal cord 26. The ultrasound endoscope 12R is attachably and detachably connected to the ultrasound processor device 14, the endoscope processor device 16, and the light source device 18 through the connectors 32a, 32b, and 32c, respectively. The air/water supply tube 34a that is connected to the water supply tank 21a, the suction tube 34b that is connected to the suction pump 21b, and the like are connected to the light source connector 32c.

The insertion part 22R includes, in order from the distal end side, the distal end portion (distal end hard portion) 40R that is formed of a hard member and that has the ultrasound observation portion 36R and the endoscope observation portion 38R, the bendable portion 42 that is consecutively provided on a proximal end side of the distal end portion 40R, is formed by connecting a plurality of bendable pieces (angle rings), and is freely bent, and the elongated and long flexible soft portion 43 that connects the proximal end side of the bendable portion 42 and the distal end side of the operating part 24.

In a case where the pair of angle knobs 29 are moved rotationally to move rotationally a pulley (not shown), an operation wire (not shown) is pulled, and the bendable portion 42 is bent in a desired direction. In this way, by operating the pair of angle knobs 29, the bendable portion 42 can be remotely bent and the distal end portion 40R can be directed in the desired direction.

In addition, in the distal end portion 40R, a balloon into which an ultrasound transmission medium (for example, water or oil) covering the ultrasound observation portion 36R is injected may be attachably and detachably mounted. Since the ultrasonic waves and the echo signals are significantly attenuated in the air, the balloon is expanded by injecting the ultrasound transmission medium therein and is brought into contact with the observation target part, whereby it is possible to eliminate air from a region between the ultrasound transducer array 50R of the ultrasound observation portion 36R and the observation target part, and to restrain attenuation in the ultrasonic waves and the echo signals.

The ultrasound processor device 14 generates and supplies an ultrasound signal (data) for making the ultrasound transducer array 50R generate an ultrasonic wave. The ultrasound processor device 14 receives and acquires an echo signal (data) reflected from an observation target part irradiated with the ultrasonic wave, by the ultrasound transducer array 50R and executes various kinds of signal (data) processing on the acquired echo signal to generate an ultrasound image that is displayed on the monitor 20.

The endoscope processor device 16 receives and acquires a captured image signal (data) acquired from the observation target part illuminated with illumination light from the light source device 18 in the endoscope observation portion 38R and executes various kinds of signal (data) processing and image processing on the acquired image signal to generate an endoscope image that is displayed on the monitor 20.

The processor devices 14 and 16 may be composed of a processor such as a personal computer (PC).

The light source device 18 generates illumination light such as white light or specific wavelength light consisting of three primary color light components of red light (R), green light (G), and blue light (B) in order to image an observation target part in a body cavity via the endoscope observation portion 38R of the ultrasound endoscope 12R and acquire an image signal. The illumination light generated in the light source device 18 is supplied to the ultrasound endoscope 12R and is propagated by a light guide (not shown) or the like in the ultrasound endoscope 12R. Next, the illumination light propagated by the light guide or the like is emitted from the endoscope observation portion 38R to illuminate the observation target part in the body cavity. That is, the light source device 18 illuminates the observation target part.

The monitor 20 receives video signals generated by the ultrasound processor device 14 and the endoscope processor device 16 and displays an ultrasound image and an endoscope image. In regard to the display of the ultrasound image and the endoscope image, only one image may be appropriately switched and displayed on the monitor 20 or both images may be displayed simultaneously. A monitor for displaying the ultrasound image and a monitor for representing the endoscope image may be separately provided, or these ultrasound image and endoscope image may be displayed in any other form.

Next, the configuration of the distal end portion and the bendable portion of the insertion part of the ultrasound endoscope will be described in detail with reference to FIG. 10.

As shown in FIG. 10, the distal end portion 40R of the ultrasound endoscope 12R is provided with the ultrasound observation portion 36R that acquires the ultrasound image, on the proximal end side, and the endoscope observation portion 38R that acquires the endoscope image, on the distal end side.

The distal end portion 40R of the ultrasound endoscope 12R comprises a cap-shaped distal end component 41a that covers a distal end of an endoscope component of the endoscope observation portion 38R on the distal end side, a proximal end-side ring 41b that is arranged on a proximal end side of the ultrasound observation portion 36R on the proximal end side, and a metal ring (not shown) made of SUS or the like that connects and fixes the distal end component 41a and the proximal end-side ring 41b. Here, the distal end component 41a and the proximal end-side ring 41b are made of a hard member, such as hard resin, and serve as an exterior member.

In addition, the cylindrical ultrasound transducer array 50R of the ultrasound observation portion 36R is wound around and integrated with an outer portion (outer periphery) of the metal ring (not shown) on the proximal end side with respect to the endoscope observation portion 38R to constitute an ultrasound probe 46R.

As is clear from the above description, the distal end portion 40R of the ultrasound endoscope 12R can be decomposed into the distal end component 41a, the proximal end-side ring 41b, and the ultrasound probe 46R including the metal ring (not shown).

In addition, the endoscope observation portion 38R consists of a treatment tool outlet port 44R, an observation window 82R, an illumination window 88R, a cleaning (air/water supply) nozzle 90R, and the like that are provided on the distal end surface.

The treatment tool outlet port (so-called forceps outlet) 44R is an outlet of a treatment tool channel (so-called forceps pipe line) (not shown) that extends to the proximal end side and that communicates with the treatment tool insertion port (so-called forceps port) 30 of the operating part 24. A treatment tool such as a forcep inserted from the treatment tool insertion port 30 of the operating part 24 into the treatment tool channel (not shown) protrudes from the treatment tool outlet port 44R, and the treatment is performed on the subject.

In the example shown in FIG. 10, the treatment tool outlet port 44R is provided in the endoscope observation portion 38R at the distal end of the distal end portion 40R, but the present invention is not particularly limited to the example shown in the drawing, and the treatment tool outlet port 44R may be provided at any position as long as it is on the distal end side of the ultrasound endoscope 12R with respect to the plurality of ultrasound transducers 48R of the ultrasound observation portion 36R.

That is, the ultrasound endoscope 12R according to the embodiment of the present invention needs to be an ultrasound endoscope in which the treatment tool outlet port 44R is arranged closer to the distal end side than the ultrasound transducer 48R.

Although not shown, an objective lens, a prism, and a solid-state imaging element are arranged behind (on the proximal end side of) the observation window 82R. The reflected light of the observation target part incident from the observation window 82R is taken in by the objective lens, the optical path is bent perpendicularly by the prism, and is imaged on the imaging surface of the solid-state imaging element. The solid-state imaging element photoelectrically converts reflected light of the observation target part transmitted through the observation window 82R, the objective lens, and the prism and imaged on the imaging surface, and outputs an imaging signal. Examples of the solid-state imaging element include a charge coupled device (CCD) and a complementary metal oxide semiconductor (CMOS).

In this way, the captured image signal output from the solid-state imaging element is transmitted to the endoscope processor device 16 by the universal cord 26 through the wiring cable (not shown) extending from the insertion part 22R to the operating part 24. The endoscope processor device 16 performs various types of signal processing and image processing on the transmitted imaging signal, and displays the processed imaging signal on the monitor 20 as an endoscope optical image.

In addition, two illumination windows 88R are provided with the observation window 82R interposed therebetween. An exit end of the light guide (not shown) is connected to the illumination window 88R. The light guide extends from the insertion part 22R to the operating part 24, and the incidence end of the light guide is connected to the light source device 18 connected through the universal cord 26. That is, the light guide extends toward the bendable portion 42, is inserted into the universal cord 26 from the operating part 24, and is finally connected to the light source connector 32c, and the light source connector 32c is connected to the light source device 18. Illumination light emitted from the light source device 18 propagates through the light guide, and the part to be observed is irradiated with the illumination light from the illumination windows 88R.

In addition, an air/water supply channel (pipe line) (not shown) is connected to the cleaning nozzle 90R. The air/water supply channel extends toward the bendable portion 42, is inserted into the universal cord 26 from the operating part 24, is connected to the light source connector 32c, and is connected to the water supply tank 21a via the air/water supply tube 34a. To clean the surfaces of the observation window 82R and the illumination windows 88R, the cleaning nozzle 90R jets air or cleaning water from the water supply tank 21a toward the observation window 82R and the illumination windows 88R through the air/water supply channel in the ultrasound endoscope 12.

Here, the up direction (UP) of the ultrasound endoscope will be described.

The upper side of the scope is the up direction (UP) of the bendable portion 42. Based on this, an observation image is created on the monitor 20.

The buttons of the operating parts 24 of the ultrasound endoscopes 12 and 12R shown in FIGS. 1 and 9, such as the air/water supply button 28a and the suction button 28b, and the bending operation knob such as the angle knob 29 are arranged on the upper side, and the upper direction in a case where the insertion parts 22 and 22R are extended and arranged in a natural state is the up direction (UP). Therefore, since the insertion parts 22 and 22R of the ultrasound endoscopes 12 and 12R shown in FIGS. 1 and 9 are bent, the direction indicated by the arrow UP is the up direction (UP), respectively.

As shown in FIG. 3, in the convex type ultrasound endoscope 12, normally, the arrangement direction of the ultrasound transducer 48 is upward, and thus, it is easy to understand, and a direction indicated by the arrow UP toward the upper side in FIG. 3 is the up direction (UP).

On the other hand, as shown in FIG. 10, in the radial type ultrasound endoscope 12R, the ultrasound transducer 48R is arranged on the entire outer periphery of the distal end, so that the optical observation system (the observation window 82R, the illumination window 88R, and the like) is related, and a direction indicated by the arrow UP toward the upper right side between the two illumination windows 88R in FIG. 10 is the up direction (UP).

Although not shown, the transesophageal echocardiography probe does not comprise buttons and has a structure of only a bending operation knob. However, since the arrangement direction of the ultrasound transducers is set upward in the same manner as in the convex type ultrasound endoscope 12, the transesophageal echocardiography probe is not different from the type comprising the optical observation system.

While the ultrasound diagnostic system according to the embodiment of the present invention has been described in detail, the present invention is not limited to the above-described embodiments, and various improvements and modifications may be made without departing from the gist of the present invention.

EXPLANATION OF REFERENCES

10, 10R: ultrasound diagnostic system
12, 12R: ultrasound endoscope
14: ultrasound processor device
16: endoscope processor device
18: light source device
20: monitor
21a: water supply tank
21b: suction pump
22, 22R: insertion part
24: operating part
26: universal cord
28a: air/water supply button
28b: suction button
29: angle knob
30: treatment tool insertion port
32a: ultrasound connector
32b: endoscope connector
32c: light source connector
34a: air/water supply tube
34b: suction tube
36, 36R: ultrasound observation portion
38, 38R: endoscope observation portion
40, 40R: distal end portion
42: bendable portion
43: soft portion
44, 44R: treatment tool outlet port
45: treatment tool channel
46, 46R: ultrasound probe
48, 48R: ultrasound transducer
50, 50R: ultrasound transducer array
54: backing material layer
56: coaxial cable
58: endoscope side memory
60: FPC
74: acoustic matching layer
76: acoustic lens
82, 82R: observation window
84: objective lens
86: solid-state imaging element
88, 88R: illumination window
90, 90R: cleaning nozzle
92: wiring cable
100: console
140: multiplexer
142: reception circuit
144: transmission circuit
146: A/D converter
148: ASIC
150: cine memory
151: memory controller
152: CPU
154: DSC
158: pulse generating circuit
160: phase matching unit
162: B mode image generation unit
164: PW mode image generation unit
166: CF mode image generation unit
168: verification mode execution unit
170: ultrasound image data generation unit
172: failure channel detection unit
174: notification unit Ra: region often used for diagnosis (transducer channel)

Rb: region not used for diagnosis very much (transducer channel)

B: cut of image

C: small circle at center of circular structure

D: line indicating up direction

L: horizontal line passing through approximate center of circular structure

UP: up direction

What is claimed is:

1. An ultrasound diagnostic system that acquires an ultrasound image of a part to be observed of a subject and performs diagnosis, the ultrasound diagnostic system comprising:

an ultrasound probe provided with an ultrasound transducer array in which a plurality of ultrasound transducers that irradiate the part to be observed with an ultrasonic wave and receive an echo signal from the part to be observed to output a detection signal are arranged; and an ultrasound processor device that executes a verification mode for verifying an operation of the ultrasound transducer array, wherein the ultrasound processor device includes a processor, the processor is configured to:

generate ultrasound image data of each pixel corresponding to each ultrasound transducer from a transmission and reception signal of each ultrasound transducer, and analyze the generated ultrasound image data to detect a failed failure transducer channel, a transducer channel is a channel that includes the ultrasound transducer and that generates the ultrasound image data of the pixel, the processor is configured to change a determination criterion for determining the failure in accordance with a condition related to an influence degree on the acquired ultrasound image, and the number of defective transducer channels, which is the determination criterion, is smaller at a position of the ultrasound transducer at which the influence degree on the ultrasound image is larger than at a position of the ultrasound transducer at which the influence degree is small.

2. The ultrasound diagnostic system according to claim 1, wherein the processor is configured to notify of a detection result.

3. The ultrasound diagnostic system according to claim 1, wherein the determination criterion includes at least either the ultrasound image data of the pixel or the number of the transducer channels.

4. The ultrasound diagnostic system according to claim 1, wherein the condition is a position of the ultrasound transducer in an arrangement direction.

5. The ultrasound diagnostic system according to claim 4, wherein the condition is a position of the ultrasound transducer that is determined depending on an apparatus type of the ultrasound diagnostic system.

6. The ultrasound diagnostic system according to claim 1, wherein the condition is at least one use mode of a user mode used by a user or a service man mode used by a service man.

7. The ultrasound diagnostic system according to claim 6, wherein, in a case where the failure is determined in each of the user mode and the service man mode, a notification is performed in each mode.

8. The ultrasound diagnostic system according to claim 1, further comprising:

a memory that stores logs of the number of detected defective transducer channels, the failure transducer channel, and at least one of a date or a date and time on which the failure transducer channel is detected, or the number of times of energization of the failure transducer channel in a case where the verification mode is executed.

9. The ultrasound diagnostic system according to claim 1, wherein diagnostic image processing for acquiring a diagnostic ultrasound image of the part to be observed is different from failure transducer channel detection image processing for generating the ultrasound image data in a case where the verification mode is executed.

10. The ultrasound diagnostic system according to claim 9, wherein, in the failure transducer channel detection image processing, processing across the plurality of ultrasound transducers is reduced as compared with the diagnostic image processing.

11. The ultrasound diagnostic system according to claim 9, wherein, in the failure transducer channel detection image processing, processing across the plurality of ultrasound transducers is not performed.

* * * * *